United States Patent [19]
White et al.

[11] Patent Number: 6,110,961
[45] Date of Patent: Aug. 29, 2000

[54] PHENOXATHIN DERIVATIVES AS INHIBITORS OF MONOAMINE OXIDASE

[75] Inventors: Helen Lyng White, deceased, late of Chapel Hill, N.C., by James White, executor; Morton Harfenist; Eric Boros, both of Chapel Hill, N.C.; Dennis Heyer, Durham, N.C.

[73] Assignee: Krenitsky Pharmaceuticals, Inc., Durham, N.C.

[21] Appl. No.: 09/254,803

[22] PCT Filed: Aug. 19, 1997

[86] PCT No.: PCT/US97/23486

§ 371 Date: Mar. 11, 1999

§ 102(e) Date: Mar. 11, 1999

[87] PCT Pub. No.: WO98/12190

PCT Pub. Date: Mar. 26, 1998

Related U.S. Application Data

[60] Provisional application No. 60/025,956, Sep. 11, 1996.

[51] Int. Cl.[7] .................. A61K 31/385; C07D 327/06
[52] U.S. Cl. ............................. 514/434; 549/16
[58] Field of Search ................. 549/16; 514/434

[56] References Cited

U.S. PATENT DOCUMENTS

| | | | |
|---|---|---|---|
| 3,409,636 | 11/1968 | Strycker | 549/16 |
| 3,440,249 | 4/1969 | Strycker | 549/16 |
| 3,642,997 | 2/1972 | Tsung-Ying et al. | |
| 4,025,635 | 5/1977 | Hodson et al. | 424/269 |
| 5,420,156 | 5/1995 | Harfenist et al. | 514/434 |

FOREIGN PATENT DOCUMENTS

| | | |
|---|---|---|
| 0 150 891 | of 0000 | European Pat. Off. |
| 0 419 157 | of 0000 | European Pat. Off. |
| WO92 04897 | of 0000 | WIPO |
| 99/13879 | 3/1999 | WIPO |

OTHER PUBLICATIONS

Depoortere, Henri, "Pharmaceutical compositions containing a monoamine oxidase inhibitor as antidepressant", CA130:247053, 1999.

*Primary Examiner*—Deborah C. Lambkin
*Attorney, Agent, or Firm*—Alston & Bird LLP

[57] ABSTRACT

The present invention provide phenoxathiin compounds useful in the prophylaxis and treatment of mental disorders, such as depression. The present invention also provides a method for treating a mammal having depression, anxiety or other conditions responsive to inhibition of MAO-A. A method of preparing the compounds of the present invention is also provided.

23 Claims, No Drawings

PHENOXATHIN DERIVATIVES AS INHIBITORS OF MONOAMINE OXIDASE

This patent is related to provisional application Ser. No. 60/025,956 filed Sep. 11, 1996. This application is a 371 of PCT/US97/23486 filed Aug. 19, 1997.

This invention relates to novel phenoxathiin derivatives, pharmaceutical formulations containing them, their use in medical therapy and processes for their preparation.

Monoamine oxidase (MAO) is the enzyme in the brain principally responsible for intraneuronal oxidation of biogenic amine neurotransmitters to inactive forms. It is understood to occur as two independent forms, normally designated MAO-A and MAO-B (White and Glassman, *J. Neurochem.*, 28, 987–997, (1977) and Tipton et al, "Monoamine Oxidase and tis Selective Inhibitors", Beckmann and Riederer, Eds., *Med. Probl. Pharmacopsychiat.*, 19 15–30, Karger, Basel (1983)). MAO inhibition has been found to elevate neurotransmitter concentrations in the brain.

MAO inhibitors are used therapeutically in the treatment of a wide variety of conditions, especially depression, particularly when characterized by anxiety, obsessional neuroses, or appetite disorders. However, a number of such compounds, for example isocarboxazid, phenelzine and tranylcypromine, are non-selective, irreversible inhibitors of the enzyme and are characterized by an undesirable side effect associated with ingestion of food or drink containing a high level of tyramine, for example, certain cheeses. When a patient receiving such a drug ingests such a product, then his blood pressure may be raised, sometimes to a dangerous level. Such patients are therefore instructed to avoid foods and beverages of this nature.

Prior art documents of interest area (A) EP 150 891; (B) WO 92 04897; (C) EP 419 157; and (D) U.S. Pat. No. 3,642,997. Patent publication (A) discloses the thioxanthen-9-ones represented by the formula

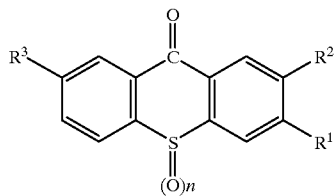

wherein n is 0, 1 or 2, and physiologically acceptable salts thereof, and teaches that they are inhibitors of MAO-A and are useful in the prophylaxis and treatment of mental disorders such as depression. Unlike the present invention, the compounds of (A) do not contain a ring oxygen.

The phenoxathiin compounds of (B) and (C) are also directed to inhibiting MAO-A, but have an alkyl substituent and lack the alkoxy substituent included in the compounds of the present invention. Publication (D) is directed to anti-inflammatory tricyclic carboxylic acid compounds.

It has now been found that a class of novel phenoxathiin compounds, which are distance from these prior art compounds, are also useful in the prophylaxis and treatment of mental disorders, such as depression. Furthermore the compounds of the present invention are advantageous in that they accumulate in the brain quickly where they may remain for a relatively long time. Thus in the rat some of the compounds of the present invention could no longer be detected in plasma 3 hours after administration but in contrast were detected in the brain for more than 3 hrs. Inhibition of brain MAO-A was observed for greater than 8 hours, although it was reversed over a 24 hour period.

Accordingly, the present invention provides a compound of formula (I) and prodrugs and physiologically functional derivatives thereof.

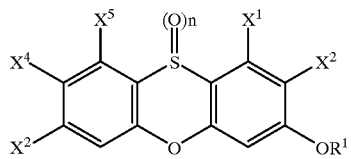

wherein n is C, 1 or 2; $R^2$ is a branched or straight chain C1-5 alkyl or C3-6 cycloalkyl optionally; substituted with hydroxyl, or one or more halogens, especially fluorine; and $X^1, X^2, X^3, X^4$, and $X^5$ are either all hydrogens or one or two of $X^1, X^2, X^3, X^4$ and $X^5$ are halogen and the remainder are hydrogens.

Preferably n is 2. Thus, the phenoxathiin 10,10-dioxides are the most preferred. Compounds of the present invention wherein n is 0, may metabolize in vivo to compounds wherein n is 1 or 2. All such compounds are of course, encompassed within the present invention.

Preferably $R^1$ is a branched or straight chain C1-3 alkyl such as methyl, ethyl, propyl and isopropyl substituted by one to four halogens, especially fluorine. When $R^1$ is ethyl or propyl, 2,2,2-trifluoroethyl and 1,1,1-trifluoroprop-2-yl are the most preferred.

Most preferred are compounds of formula I where n is 0, 1 or 2 and $R^1$ is a branched or straight chain C1-3 alkyl, and most preferably where n is 2 and $R^1$ is isopropyl.

One or two of $X^1, X^2, X^3, X^4$ and $X^5$ may be halogen.
Examples of halogens include bromine, chlorine and fluorine, with fluorine being the most preferred.

Examples of compounds according to the present invention are listed in Table 1.

Paticularly preferred compounds of the present invention include:
3-(2,2,2-trifluoroethoxy)phenoxathiin 10,10-dioxide
3-(2,2-(difluoro)-1-(difluoromethyl)ehtoxy)phenoxathiin 10,10-dioxide
(rac)-3-(1-(difluoromethyl)ethoxy)phenoxathiin 10,10-dioxide
(rac)-3-(2-fluoro-1-(trifluoromethyl)ethoxy)phenoxathiin 10,10-dioxide
(rac)-b 3-(1-(fluoromethyl)ethoxy)phenoxathiin 10,10-dioxide
(rac)-2-(3-phenoxathiinyloxy)-2-trifluoromethyl)ethanol S,S-dioxide
3-(1-(fluoromethyl)ethenyloxy)phenoxathiin 10,10-dioxide
3-isopropoxyphenoxathiin 10,10-dioxide
7-fluoro-3-isopropoxyphenoxathiin 10,10-dioxide
(rac)-2-(3-phenoxathiinyloxy)propanol S,S-dioxide
1,7-diflouoro-3-isopropoxyphenoxathiin 10,10-dioxide
1-fluoro-3-isopropoxyphenoxathiin 10,10-dioxide
2,7-difluoro-3-isopropoxyphenoxathiin 10,10-dioxide
9-fluoro-3-isopropoxyphenoxathiin 10,10-dioxide
(rac)-3-(2,2,2-trifluoro-1-methylethoxy)phenoxathiin 10,10-dioxide
[Alternative name=3-(1-(trifluoromethyl)ethoxy) phenoxathiin 10,10-dioxide]
3-[2-fluoro-1-(fluoromethyl)ethoxy]phenoxathiin, 10,10-dioxide
(R*)-3-(2,2,2-trifluoro-1-methylethoxy)phenoxathiin 10,10-dioxide
(S*)-3-(2,2,2-trifluoro-1-methylethoxy)phenoxathiin 10,10-dioxide 3-fluoro-7-(2,2,2-trifluoroethoxy)phenoxathiin 10,10-dioxide The most preferred compounds of the invention are:

3-(2,2,2-trifluoroethoxy)phenoxathiin 10,10-dioxide 3-(2,2-(difluoro)-1-(difluoromethyl)ethoxy)phenoxathiin 10,10-dioxide 3-isopropoxyphenoxathiin 10,10-dioxide 7-fluoro-3-isopropoxyphenoxathiin 10,10-dioxide (rac)-2-(3-phenoxathiinyloxy)propanol S,S-dioxide 1,7-difluoro-3-isopropoxyphenoxathiin 10,10-dioxide 1-fluoro-3-isopropoxyphenoxathiin 10,10-dioxide (rac)-3-(2,2,2-trifluoro-1-methylethoxy)phenoxathiin 10,10-dioxide

[Alternative name=3-(1-trifluoromethyl)ethoxy) phenoxathiin 10,10-dioxide]

($R^*$)-3-(2,2,2-trifluoro-1-methylethoxy)phenoxathiin 10,10-dioxide ($S^*$)-3-(2,2,2-trifluoro-1-methylethoxy)phenoxathiin 10,10-dioxide 3-fluoro-7-(2,2,2-trifluoroethoxy)phenoxathiin 10,10-dioxide It will be appreciated that the compounds of formula (I) can exist in various geoisomeric forms and as mixtures thereof in any proportions. Thus the invention includes all enantiomeric and diastereomeric forms of the compounds of formula (I) either individually or admixed in any proportion.

Included within formula (I) are compounds wherein one or more carbon centers is/are chiral. The present invention includes within its scope each possible optical isomer substantially free from, i.e., associated with less than 5% of, any other optical isomer(s), as well as mixtures of one or more optical isomers in any proportions, including racemic mixtures thereof.

It will be evident to a skilled person that certain compounds of formula (I) can exist in enantiomeric forms according to the direction of rotation of plane polarized light when passed through a sample of the compound. Individual optical isomers as well as mixtures of each isomers in any proportions are within the scope of the invention.

The present invention also includes prodrugs and metabolites of the compounds of formula I. By prodrugs is meant those compounds which are metabolized in vivo to form a compound of formula I. By metabolite is meant any compound resulting directly or indirectly from the in vivo metabolism of a compound of formula I.

Depression states in which the compounds are particularly useful are those defined in the *Diagnostic and Statistical Manual of Mental Disorders,* third edition (DSM III), American Psychiatric Association, Washington, D.C. (1980), (DSM III, 296.2X to 296.6X and 301.13), including that characterized by anxiety or obsessional neuroses (DSM III, 300.40), or atypical depression including depression in the elderly or symptoms of early senility, especially symptoms relating to sociability and quality of life (DSM III, 296.70 and 296.82), e.g., accompanied by a personality disorder.

Other therapeutic uses for the compounds include treatment of post-traumatic stress disorder (DSM III, 300.30), anxiety states (DSM III, 300.00, 300.01, 300,02, 300.21, 300.22, 300.23 and 300.29), e.g., which are accompanied in an acute phase by panic attacks with or without phobia (DSM III 300.21), phobia (DSM III 300.23 and 300.29), appetite disorders, e.g., bulimia (DSM III, 307.51) and anorexia (DSM III, 307.10), and borderline personality disorder (DSM III, 301.83). Still further therapeutic uses for the compounds include treatment of headaches, e.g., migraine, muscle contraction and mixed (i.e., combination of migraine and muscle contraction) headaches.

The present invention thus provides a method for the treatment of mental disorders, in mammals (eg. humans) including depression, anxiety, and other conditions enumerated above which are responsive to inhibition of MAO-A which comprises administering to said mammal an effective treatment amount of a compound of formula (I).

The compounds according to the present invention are not only potent and selective inhibitors of MAO-A, but are also reversibly bound to MAO-A as shown by their removal by dialysis from their complexes with MAO-A. Furthermore, no pharmacologically significant increase in response (elevation of blood pressure) has been observed in test animals which have been given oral antidepressant doses of compounds of formula (I) prior to orally ingested tyramine.

The compounds may be administered by, for example, the oral, transdermal, rectal or parenteral route. In general, the compounds may be administered for the treatment of each of the disorders stated hereinabove, including depression, with the dosage range of about 0.1 mg to about 50 mg per kg of human bodyweight per day, preferably about 1 mg to about 40 mg per kg of human bodyweight per day and optimally about 1 to 10 mg per kg of human bodyweight per day, although the precise dosage will naturally depend upon a number of clinical factors, for example, the age of the recipient, the route of administration and the condition under treatment and its severity, and upon the identity of the compound employed: for administration by the oral route, a dosage regimen of 0.3 to 30 mg per kg per day, preferably 2 to 20 mg per kg per day and optimally about 5 mg per kg per day, may be used. The desired daily dose is preferably given as one to three or more subdoes administered at appropriate intervals during the day. These subdoses may be presented in unit dosage form each containing, for example, from 50 to 500 mg, preferably 200 mg, of the compound.

While it is possible to administer the compounds as the raw chemicals, it is highly desirable to administer them in the form of a pharmaceutical formulation.

The present invention further provides a pharmaceutical formulation comprising a compound of formula (I) or prodrugs and metabolites thereof together with an acceptable carrier therefor. The carrier should be acceptable in the sense of being compatible with the other ingredients and not deleterious to the recipient thereof. The formulations may be adapted for oral, parenteral, transdermal or rectal administration inter alia.

The formulations may conveniently be presented in unit dosage form and may be prepared by any of the methods well known in the art of pharmacy. Such methods include the step of bringing into association the compound of formula (I) (the active ingredient) with the carrier which may comprise one or more accessory ingredients. In general the formulations are prepared by uniformly and intimately bringing into association the active ingredient with liquid carriers of finely divided solid carriers or both, and then, if necessary, shaping or encapsulating the product.

Formulations of the present invention suitable for oral administration may be presented as discrete units such as capsules, cachets or tablets each containing a predetermined amount of the active ingredient; as a powder or granules; as a solution or a suspension in a liquid such as labrafil M1944CS (Gattefosse) or Cremophor RH40 (BASF) or a non-aqueous liquid; or as an oil-in-water liquid emulsion or a water-in-oil liquid emulsion.

A tablet may be made by compression or molding, optionally with one or more accessory ingredients. Compressed tablets may be prepared by compressing i a suitable machine the active ingredient in a free-flowing form such as a powder or granules, optionally mixed with a binder, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for rectal administration may be presented as a suppository with the usual carriers such as cocoa butter.

Formulations suitable for parenteral administration include aqueous sterile injection solutions which may contain antioxidants, buffers, bacteriostats and solutes which render the formulation isotonic with the blood of the intended recipient; and aqueous and nonaqueous sterile suspensions which may include suspending agents. The formulations may be presented in unit dose or multidose containers, for example sealed ampoules and vials, and may be stored in a freeze-dried (lyophilized) condition requiring only the addition of the sterile liquid carrier, for example PEG 400:ethanol mixtures, immediately prior to use. Extemporaneous injection solutions and suspensions may be prepared from sterile powders, granules and tablets of the kind previously described.

Preferred unit dosage formulations are those containing a daily dose or unit daily subdose, as hereinabove recited, or an appropriate fraction thereof, of the active ingredient.

It should be understood that, in addition to the ingredients particularly mentioned above, the formulations of this invention may include other agents conventional in the art having regard to the type of formulation in question, for example, those suitable for oral administration may include flavoring agents.

The compounds of formula (I) may be prepared by those methods known in the art for the synthesis of compounds of analogous structure and in this regard reference is made by way of illustration only, to the following reference: Harfenist, McGee and White, *J. Med Chem.*, 34, 2931–2933 (1991).

Briefly, the method comprises treating a substituted orthohydroxy-thiophenol, where the substituent is a preferably protected e.g. acylated hydroxy- or alkoxyl or halo (preferably bromo or fluoro) or a group conertible to hydroxy or alkoxy by known means with an ortho-nitrohalobenzene (optionally substituted with one or more fluorines atoms) in the presence of a basic medium. The resulting diaryl sulfide is either oxidized to the corresponding sulfone and the resulting sulfone cyclised to the phenoxathiin 10,10-dioxide with base, or the diaryl sulfide is cyclised to the phenoxathiin and then oxidized to its 10,10-dioxide.

Example 1

Pharmaceutical Formulations

In the following formulation examples, 'Active Ingredient' means a compound of formula (i).

A - 100 mg Compression Coated Tablet

|  | Ingredients | Amount per Tablet |
|---|---|---|
| Core | Active Ingredient | 100 mg |
|  | Cornstarch | 25 mg |
|  | Magnesium Stearate | 2 mg |

-continued

A - 100 mg Compression Coated Tablet

|  | Ingredients | Amount per Tablet |
|---|---|---|
| Coating | Coating Lactose | 320 mg |
|  | Cornstrach | 50 mg |
|  | Gelatin | 6 mg |
|  | Magnesium Stearate | 4 mg |

The Active Ingredient and starch are granulated with water and dried. Magnesium stearate is added to the dried granules. Lactose and starch are granulated with a 10% w/v aqueous solution of gelatin and dried. Magnesium stearate is added to the dried granules. The granulated core is compressed with the granulated coating in a conventional compression molding machine.

B - 200 mg Capsule

| Ingredient | Amount Per Capsule |
|---|---|
| Active Ingredient | 200 mg |
| Lactose | 200 mg |
| Talc | 40 mg |

The Active Ingredient, lactose and talc are brought into intimate admixture with one another and 440 mg of the resultant mixture is introduced into a size 0 hard gelatin capsule C - 100 mg Capsule

| Ingredients | Amount Per Capsule |
|---|---|
| Active Ingredient | 100 mg |
| Lactose | 100 mg |
| Cornstarch | 100 mg |
| Magnesium Stearate | 10 mg |

The ingredients are mixed together until homogeneous and 310 mg of the resulting mixture filled into each hard gelatin capsule.

D - 100 mg Capsule

| Ingredients | Amount Per Capsule |
|---|---|
| Active Inqredient | 100 mg |
| Gelucire 37/02 | 400 mg |
| PEG 3350 | 50 mg |

The Gelucire 37/02 is melted by heating at 90° C. the PEG 3350 is added, and the mixture is stirred to give a uniform melt. While monitoring the temperature at 90° C., the Active Ingredient is added and the mixture stirred to give a homogeneous mixture. The mixture is added to size 0 hard gelatin capsules, cooled and capped. Gelucire 37/02 is a trademark of Gattefosse Corporation of Elmsford, N.Y. for hydrogenated polyglycolized glycerides prepared from $C_{10-18}$ hydrogenated fatty acids, glycerol and PEG 300. PEG 300 poly(ethylene glycol) of approximate molecular weight 300; PEG 3350 is poly(ethylene glycol) of approximate molecular weight 3350.

E - 100 mg Capsule

| Ingredients | Amount Per Capsule |
|---|---|
| Active Ingredient | 20 mg |
| Labrafil M 1944 CS | 640 mg |

The Labrafil is heated to about 70° C., and the Active Ingredient is then added with stirring to give a homogeneous mixture. The mixture is added to size 0 hard gelatin capsules, cooled and capped. Labrafil M1944 CS is a trademark of Gattefosse Corporation of Elmsford, N.Y. for unsaturated polyglycolized glycerides prepared from apricot kernel oil (PEG 300 or PEG 6).

F - 500 mg Tablet

| Ingredients | Amount Per Tablet |
|---|---|
| Active Ingredient | 500 mg |
| Cornstarch | 100 mg |
| Microcrystalline Cellulose | 75 mg |
| Magnesium Stearate | 5 mg |
| Granulated polyvinylpyrrolidone (10% w/v in 50% w/v aqueous ethanol) | 10 mg |

The Active Ingredient, corn starch and microcrystalline cellulose are mixed together, and granulated with the alcoholic polyvinylpyrrolidone. The resulting granules are dried, and compressed to produce tablets, each tablet having a weight of approximately 690 mg.

G - Suppository

| Ingredients | Amount Per Suppository |
|---|---|
| Active Ingredient | 200 mg |
| Suppository | q.s. to 2 g |

The Active Ingredient in fine powder form is dispersed into a little of the molten Suppository Base at 50° C. The dispersion is incorporated into the bulk of the base at the same temperature, allowed to cool at 42°–45° C. poured into suitable 2 g suppository molds and allowed to set at 15°–20° C. Suitable suppository bases are Massa Esterinum C (Henkel International, Dusseldorf, Germany) and Witten H Suppository Compound.

H - Dispersible Tablet

| Ingredients | Amount Tablet |
|---|---|
| Active Ingredient | 200 mg |
| Corn Starch | 40 mg |

-continued

H - Dispersible Tablet

| Ingredients | Amount Tablet |
|---|---|
| Primojel (Trade name: sodium starch glycollate (125#m powder)) | 50 mg |
| Dicalcium Phosphate Dihydrate | 50 mg |
| Sodium Carboxymethyl Cellulose | 2 mg |
| Sodium Saccharin | 5 g |
| Microcrystalline Cellulose | 50 mg |
| Magnesium Stearate | 3 mg |

The Active Ingredient, half of the corn starch, the Primojel and dicalcium phosphate dihydrate are mixed together and then granulated with a solution of sodium carboxymethyl cellulose and sodium saccharin in a suitable volume of 50% ethyl alcohol. The granules are dried, the remaining corn starch, the microcrystalline cellulose and the magnesium stearate are blended-in and the resulting mixture compressed into tablets.

Example 2

Bilogical Activity

A. Monoamine Oxidase Inhibition

MAO was assayed with [$^3$H]serotonin (0.2 mM, 5 Ci/mole) and [$^{14}$C]β-phenethylamine (10 μM, 3 Ci/mole) as substrates in a double-label assay (white and Glassman, *J. Neurochem.* 29:987–97 (1977)). Under these conditions, serotonin is selectively metabolized by MAO-A and β-phenethylamine by MAO-B.

For studies of the kinetic mechanism of inhibition, the above method was used except that a single substrate, serotonin or tyramine, was varied over a 10-fold concentration range that included the $K_m$ concentration. When tyramine was used as substrate, the extract was pretreated with deprenyl (1 μM) to inhibit all MAO-B activity. MAO-A activity was determined in the absence and presence of the compound under test at each substrate concentration in duplicate or triplicate assays.

Compounds of formula (I) produced a potent selective inhibition of MAO-A in mitochondrial extracts of rat brain, the $IC_{50}$s (concentration producing 50% inhibition) being shown in Table I. This inhibition was competitive vs. the substrates serotonin or tyramine.

The results are shown in Table 1 with the $IC_{50}$ being the concentration providing 50% inhibition. No significant inhibition of MAO-B was found with these compounds.

TABLE I

MAO-A Inhibition (rat brain)

| Cmpd. Prepared as No. Described in | Compound Name | in vitro IC$_{50}$, uM | Example(s) |
|---|---|---|---|
| 1. | 1-fluoro-3-isopropoxyphenoxathiin 10,10-dioxide | 0.0011 | 23–27 |
| 2. | 3-ethoxyphenoxathiin 10,10-dioxide | 0.002 | 34 |
| 3. | 3-propoxyphenoxathiin 10,10-dioxide | 0.0025 | 35 |
| 4. | 1,2-difluoro-3-isopropoxyphenoxathiin 10,10-dioxide | 0.003 | 12–17 |
| 5. | 3-isopropoxyphenoxathiin 10,10-dioxide | 0.0034 | 3–8 |
| 6. | (R)-3-(1-methylpropoxy)phenoxathiin 10,10-dioxide | 0.004 | 11 |
| 7. | (S)-3-(1-methylpropoxy)phenoxathiin 10,10-dioxide | 0.004 | 11 |
| 8. | 3-butoxyphenoxathiin 10,10-dioxide | 0.005 | 36a |
| 9. | 7,8-difluoro-3-isopropoxyphenoxathiin-10,10-dioxide | 0.006 | 28–32 |
| 10. | 9-fluoro-3-isopropoxyphenoxathiin 10,10-dioxide | 0.008 | 18–22 |
| 11. | 7-fluoro-3-isopropoxyphenoxathiin 10,10-dioxide | 0.009 | 9 |
| 12. | 2-fluoro-3-isopropoxyphenoxathiin 10,10-dioxide | 0.012 | 28–32 |
| 13. | (rac)-3-(1-methylpropoxy)phenoxathiin-10,10-dioxide | 0.014 | 11 |
| 14. | 3-methoxyphenoxathiin 10,10-dioxide | 0.02 | 33 |
| 15. | 3-tert-butoxyphenoxathiin 10,10-dioxide | 0.026 | 10 |
| 16. | 2,7-difluoro-3-isopropoxyphenoxathiin 10,10-dioxide | 0.035 | 28–32 |
| 17. | 3-(pentyloxy)phenoxathiin 10,10-dioxide | 0.055 | 36 |
| 18. | (rac)-2-(3-phenoxathiinyloxy)propanol S,S-dioxide | 0.02 | 37 |
| 19. | 1,7-difluoro-3-isopropoxyphenoxathiin 10,10-dioxide | 0.005 | 38–45 |
| 20. | (rac)-3-(2,2,2-trifluoro-1-methylethoxy) phenoxathiin-10,10-dioxide | 0.005 | 46 |
| 21. | (S)-(+)-2-(3-phenoxathiinyloxy)propanol S,S-dioxide | 0.070 | 47 |
| 22. | 3-(2,2,2-trifluoroethoxy)phenoxathiin 10,10-dioxide | 0.008 | 55 |
| 23. | 3-[2-fluoro-1-(fluoromethyl)ethoxy] phenoxathiin-10,10-dioxide | 0.002 | 56 |
| 24. | 3-(2,2-(difluoro)-1-(difluoromethyl) ethoxy)phenoxathiin-10,10-dioxide | 0.0035 | 57 |
| 25. | (rac)-3-(1-(difluoromethyl)ethoxy) phenoxathiin-10,10-dioxide | 0.0018 | 58 |
| 26. | (rac)-3-(2-fluoro-1-(trifluoromethyl) ethoxy)phenoxathiin-10,10-dioxide | active | 60 |
| 27. | (rac)-3-(1-(fluoromethyl)ethoxy) phenoxathiin-10,10-dioxide | active | 61 |
| 28. | (rac)-2-(3-phenoxathiinyloxy)-2-(trifluoromethyl)ethanol-S,S-dioxide | 0.005 | 59 |
| 29. | (R*)-3-(2,2,2-trifluoro-1-methylethoxy) phenoxathiin-10,10-dioxide | 0.002 | 62 |
| 30. | (S*)-3-(2,2,2-trifluoro-1-methylethoxy) phenoxathiin-10,10-dioxide | 0.014 | 62 |
| 31. | 3-fluoro-7-(2,2,2-trifluoroethoxy) phenoxathiin-10,10-dioxide | active | 64 |

B. Effects on Blood Pressure Response to Oral Tyramine

Compounds of formula (I) were tested for effects on the pressor response induced by orally administered tyramine in a conscious, unrestrained rat model. The method involves direct measurement of mean arterial blood pressure from a cannula implanted in a carotid artery and exteriorized through a small incision in the back of the neck. Peak changes in the pressor response following tyramine (p.o.) in animals pretreated with test compound (p.o.) were compared with changes seen in animals pretreated with either the known MAO inhibitor, phenelzine, (p.o.) or vehicle (water) alone.

To compare effects at equipotent doses that are relevant to antidepressant activity, either the test compound or phenelzine was given in a single oral dose that produced approximately 80% inhibition of brain MAO-A by the time of tyramine administration 3 hours later. Under these conditions, liver MAO-A was inhibited by 90% or more by phenelzine.

Rats pretreated with vehicle alone exhibited blood pressure elevations at relatively high doses of tyramine, i.e. above 27 mg/kg. Compound of formula (I) (at doses giving at least 80% MAO-A inhibition in brain) did not cause a statistically significant increase in the pressor response to tyramine at threshold tyramine doses (15 mg/kg), while phenelzine (50mg/kg., p.o.) caused a 57.5 (±3.6) % increase in mean arterial blood pressure in response to the same dose of tyramine.

Example 3

6-Isopropoxy-1,3-benzoxathiol-2-one

| Materials | M.W. | moles | grams | liters |
|---|---|---|---|---|
| 6-hydroxy-1,3-benzoxathiol-2-one | 168.27 | 1.23 | 207.0 | |
| potassium carbonate, anhydrous | 138.21 | 2.46 | 340.0 | |
| 2-iodopropane | 169.99 | 3.69 | 627.3 | 0.37 |
| N,N-dimethylformamide, anhydrous | | | | 1.0 |
| acetic acid, glacial | 60.05 | 3.76 | | 0.215 |
| ethyl acetate | | | | 1.45 |
| hexane | | | | 1.75 |
| water | | | | 3.0 |
| sodium chloride solution, saturated | | | | 0.2 |
| magnesium sulfate, anhydrous | | | | |

Theoretical Yield: 258.6 g

Procedure:

To a 3-L three-necked flask fitted with a nitrogen inlet, 500 ml addition funnel, and air stirrer was added anhydrous potassium carbonate (Note 1), 6-hydroxy-1,3-benzoxathiol-2-one, dry dimethylformamide, and 2-iodopropane. The mixture was stirred for 15.5 hours at ambient temperature and then chilled in an ice bath. Acetic acid was added dropwise (Note 2) followed by ethyl acetate (1 L). The mixture was filtered and the cake washed with ethyl acetate (3×150 mL). The filtrate was transferred to a 4-L separatory funnel, hexane (250 mL) was added to aid in the phase separation, and the solution washed with water (1 L, then 4×500 mL) and saturated sodium chloride solution. The organic phase was then dried over magnesium sulfate, filtered, and the solvent evaporated to give 253.3 g of a yellow oil which, by HPLC, contained about 84% product, 9% unalkylated starting material, and 6% of a dialkylated impurity. The oil was dissolved in hexane (1.5 L) at 55° C., seeded with some of the starting material, cooled to room temperature, and then chilled in an ice bath. The precipitate was filtered, washed with a little hexane, and dried to give 16.10 g of unreacted starting material (7.8% recovery). Evaporation of the hexane filtrate left a yellow oil containing, by HPLC, approximately 90% product, 2.5% unreacted starting material, and 6.6% dialkylated impurities. This material is suitable for subsequent reactions without further purification.

HPLC conditions: Phenomenex Ultracarb (30) 5μ ODS column using 790.210:0.2:0.1 MeOH/H$_2$O/Et$_3$N/TFA at 0.8 mL/min and 254 nm. Starting material RT 5.5 min; product RT 15.5 min; dialkylated impurity RT 21 min. A small amount of trialkylated impurity is sometimes seen at RT 49 min.

Note 1: The potassium carbonate was crushed with a mortar and pestle and dried in a vacuum oven at 110° C. overnight. The more water present in the reaction, the more dialkylated and trialkylated impurities are formed.

Note 2: The acetic acid can be added rather quickly at first, but toward the end of the addition foaming becomes a problem. Slow addition at this point helps to control the foaming.

Example 4

2-Hydroxy-4-isopropoxy-2'-nitrodiphenylsulfide

| Materials | M.W. | moles | grams | liters |
|---|---|---|---|---|
| 6-isopropoxy-1,3-benzoxathiol-2-one | 210.25 | | 1.03 | 216.43 |
| sodium hydroxide, 3N | | | 2.36 | 0.785 |
| tetrahydrofuran | | | | 1.5 |
| sodium borohydride | 37.83 | 0.12 | 4.5 | |
| 2-bromonitrobenzene | 202.01 | 1.05 | 212.11 | |
| HCL, conc. | | 1.32 | | 0.11 |
| ethyl acetate | | | | 0.70 |
| hexane | | | | 3.5 |
| water | | | | 0.40 |
| sodium chloride solution, saturated | | | | 0.15 |
| magnesium sulfate, anhydrous | | | | |

Theoretical Yield: 314.51 g

Procedure:

To a 3-L flask (fitted with reflux condenser, an air stirrer and, a nitrogen inlet) was added 6-isopropoxy-1,3-benzoxathiol-2-one, (Example 3) tetrahydrofuran, and 3N sodium hydroxide. The mixture was refluxed for 6.75 hours while monitored by HPLC (Note 1). The mixture was then chilled in an ice bath and sodium borohydride was added in portions (3×1.5 g) at ca 15 minute intervals (Note 2). Next was added the 2-bromonitrobenzene as a neat liquid. The mixture was stirred overnight and checked by TLC in the morning (Note 3). Concentrated HCL was added and the biphasic mixture stirred for 1.5 hours. The phases were separated and the aqueous phase extracted with ethyl acetate (ca 200 mL). The combined organics were washed with water (400 mL). To aid in phase separation, hexane (200 ml) and saturated sodium chloride solution (50 mL) were added. The phases were separated and the organics washed with saturated sodium chloride (100 mL) and dried over magnesium sulfate. Evaporation of solvents left a damp yellow solid (421 g). This was dissolved in boiling ethyl acetate (500 mL) and diluted at the boil with hexane (ca 3.3 L). The solution was seeded with product, cooled to room temperature, and then chilled in the cold room overnight. The resulting yellow solid was filtered, washed with hexane, and dried in the vacuum oven at room temperature overnight.

A small amount of a second crop was obtained by evaporating the mother liquors and dissolving the resulting oil in ethyl acetate (100 mL) at 60° C. and adding hexane (ca 1200 mL). Seeding and chilling overnight gave an additional 11.0 g of product (3.5%).

Note 1: HPLC conditions: Phenomenex Ultracarb (30) 5μ ODS using 790:210:0.2:0.1 MeOH/H$_2$O/TFA/Et$_3$N at 0.8 mL/min and 254 nm. Starting material RT 15.0 min, product RT 8.0 min. A disulfide impurity and perhaps an unidentified impurity co-eluate at RT 20.2 min. After six hours at reflux, the amounts by HPLC are approximately: starting material, 2.6%; product, 80.7%; RT 20 impurities, 13.1%.

Note 2: Usually the addition of sodium borohydride reduces the amount of disulfide as well as eliminating a yellow color from the reaction solution. Although the yellow color was removed from this reaction, the amount of the RT 20 impurities did not seem to change by HPLC.

Note 3: Two TLC systems have been developed. System 1: Silica gel plates using 3:2 hexane/ethyl acetate. Starting material, Rf 0.83; product, Rf 0.66 (visible yellow spot); 2-bromonitrobenzene, Rf 0.78. The disulfide impurity has the same Rf as the product in this system. System 2: RP C-18 plates using 75:25:6 drops MeOH/H$_2$O/HOAc. Product, Rf 0.22; 2-bromonitrobenzene, Rf 0.40; disulfide impurity; Rf 0.70.

Example 5

2-Hydroxy-4-isopropoxy-2'-nitrodiphenylsulfone

| Materials | M.W. | moles | grams | liters |
|---|---|---|---|---|
| 2-hydroxy-4-isopropoxy-2'-nitrodiphenylsulfide | 305.35 | 0.732 | 223.37 | 1.0 |
| acetic acid, glacial peracetic acid, 32% | | 1.95 | | 0.41 |
| hydrogen peroxide, 30% | | 0.25 | | 0.025 |
| water | | | | 9.0 |

Theoretical Yield: 246.77 g

Procedure:

To a 3-L flask-fitted with an air stirrer, addition funnel, and thermometer was added 2-hydroxy-4-isopropoxy-2'-nitrodiphenylsulfide (Example 4) and acetic acid. The suspension was heated to 50° C. and the hydrogen peroxide added all at once (Note 1). The peracetic acid was added dropwise. The exotherm raised the temperature to 65° C., so addition was stopped while the reaction was chilled to 40° C. water bath. After 30 minutes the reaction temperature was 57° C. (bath temperature now at 50°). The bath was cooled to 35° C., and the reaction temperature dropped slowly to 38° C. over 30 minutes. TLC in System 1 at this point indicated that there was no sulfide remaining. HPLC indicated approximately a 62:38 ratio of sulfoxide to sulfone. The reaction was further monitored by TLC in System 2. After ca five hours at 35–45° C., only a trace of the sulfoxide was seen by TLC. At this point, some crystals were present in the reaction. Water (1 L at 50° C.) was added and the mixture transferred to a 4-L Erlenmeyer. The mixture was then stirred and diluted to the 4-L mark with water (6×1 L). The product was dried in a vacuum oven at 55° C. overnight until the odor of acetic acid could not be detected.

Chromatography Systems:

HPLC: Phenomenex Ultracarb (30) 5µ ODS using 680:320:0.2:0.1 MeOH/H$_2$O/TFA/Et$_3$N at 0.8 mL/min and 254 nm. Sulfoxide RT 11.4 min; sulfone RT 10.5 min. these two are not well resolved, and as the reaction proceeds, the sulfoxide peak is gradually absorbed into the sulfone peak.

Note 1: Normally only peracetic acid is used. In this reaction, not enough peracetic acid was available so hydrogen peroxide was used to make up the three equivalents. In some smaller scale reaction, only hydrogen peroxide in acetic acid was used. These oxidations were much slower than the ones with peractic acid.

Example 6

3-Isopropoxyphenoxathiin10,10-dioxide

| Materials: | M.W. | moles | grams | liters |
|---|---|---|---|---|
| 2-hydroxy-4-isopropoxy-2'-nitrodiphenylsulfone | 337.35 | 0.617 | 208.17 | |
| sodium hydride, 60% oil dispersion | 24.00 | 0.74 | 29.62 | |
| N,N-dimethyformamide, anhydrous (DMF) | | | | 1.1 |
| Methanol | | | | 0.25 |
| water | | | | 2.75 |
| methylene chloride | | | | 1.6 |
| sodium hydroxide, 1N | | | | 0.75 |
| sodium chloride solution, saturated | | | | 0.10 |
| magnesium sulfate | | | | |
| silica gel | | | | |
| isopropanol | | | | 0.975 |
| hexane, for washings | | | | |

Theoretical Yield: 179.14

Procedure:

To a 3-L flask fitted with nitrogen inlet, air stirrer, addition funnel, and temperature controller was added the sodium hydride. This was washed with three portions of hexane to remove the oil. Each washing was allowed to settle and the supernatant removed by pipette each time. Then dimethylformamide (100 mL) was added and stirring began. The 2-hydroxy-4-isopropoxy-2'-nitrodiphenylsulfone (see Example 5) was dissolved in DMF (1 L) and added dropwise slowly. The temperature rose to 48–49° C. during the addition. The mixture was then heated and stirred at 80° C. for 1.75 hours. The reaction may be monitored by TLC. The mixture was then concentrated to a volume of 200–300 mL on the rotary evaporator using a 70° C. water bath. Hot methanol (250 mL) was then added and some solids were obtained. The suspension was then stirred at 50–60° C. while warm water (750 mL, 60° C.) was added. The dark yellow-black suspension was chilled overnight in the cold room. The resulting yellow-brown solids were filtered, washed with water (2×500 mL), and air dried to give a damp cake (weight ca 198 g). The cake was dissolved in methylene chloride (800 mL) and washed successively with sodium hydroxide (3×250 mL), water (2×500 mL), and saturated sodium chloride solution (100 mL). The solution was dried over magnesium sulfate and filtered to give ca 1 L of yellow-orange solution. This was then filtered through a bed of silica gel (the bed occupied approximately ¾ of a 350 mL scintered glass funnel and the bed washed with approximately 600 mL methylene chloride. The light yellow filtrate was evaporated to give a light yellow solid (158.0 g, ca 97% by HPLC). The solid was dissolved in refluxing isopropanol (500 mL. Cooling to room temperature gave a precipitate. The suspension was chilled with stirring in an ice bath. The solids were filtered, washed with cold isopropanol (250 mL, 175 mL), and then hexane. The product was dried overnight in a vacuum oven at 66° C. Purity by HPLC was 99.8% AUC. M.p. 91–92° C.

Chromatography:

TLC was on silica gel plates using 3:2 hexane/ethyl acetate. Starting material, Rf 0.20; product Rf 0.61. HPLC was on Phenomenex Ultracarb (30) 5µ and ultracarb ODS using 790:2,10:0.2:0.1 MeOH/H$_2$O/TFA/Et$_3$N at 0.8 ml/min and 254 nm. Product RT 11.3 min.

Example 7

3-Hydroxphenoxathiin 10,10-dioxide

A stirred solution of 29.4 gm of 3-methoxyphenoxathiin 10,10-dioxide, 5.2 gm of tetrabutylammonium bromide (Aldrich Chemical Co.), and 500 mL of 48% aqueous HBr was refluxed in a 1 liter flask for 6 hours. It was allowed to stir overnight at room temperature and was then refluxed for one additional hour. The contents were cooled to room temperature, and a solid filtered off and washed with waster. There was obtained 26.43 gm of 3-hydroxyphenoxathiin 10,10-dioxide. This was of sufficient purity to be used for further synthetic work. Proton NMR was consistent with the structure. Recrystallization of 0.5 gm from EtOAc/Hexane yielded 0.32 gm, m.p.=213–215°.

Anal. Calcd for $C_{12}H_8SO_2$, MW 216.25: C,58.05; H,3.25; S,12.91. Found C,58.16; H,3.20; S, 12.83.

Example 8

3-Isopropoxyphenoxathiin 10,10-dioxide

An alternative synthesis:

A mixture of 1.00 gm (0.0043 mole) of 3-hydroxyphenoxathiin 10,10-dioxide (Example 7) 1.48 gm (0.0107 mole) of anhydrous granular potassium carbonate, 5.5 mL of 2-iodopropane (Aldrich Chemical Co.), and 60 mL of acetone were stirred overnight. The acetone was removed under water pump vacuum and the residue mixed with methylene chloride and filtered. The filtrate was washed with 2×200 mL of water and dried over magnesium sulfate. The solvent was removed under water pump vacuum to give an oil. Some hexane was added to the oil and the mixture heated on a steam bath. This gave a white solid which was recrystallized from ethyl acetate/hexane to yield 0.75 gm of 3-isopropoxyphenoxathiin 10,10-dioxide, m.p. 94–95°.

Anal. Calcd for $C_{15}H_{14}O_4S$, MW 290.35: C, 62.05; H, 4.87; S, 11.04. Found C, 61.97; H, 4.86; S, 10.96.

Example 9

3-Fluoro-7-isopropoxyphenoxathiin 10,10-dioxide [7-Fluoro-3-isoproxyphenoxathiin 10,10-dioxide]

A mixture of 2.33 gm (12.1 mmol) of 5-isoproxy-2-mercaptophenol, 1.89 gm (12.1 mmol) of 2.5-difluoronitrobenzene (Aldrich Chemical Co.) m, 2.86 gm (24.24 mmol) of potassium tert-butoxide (95%), and 40 mL of 1-methyl-2-pyrolidinone was heated under $N_2$ at 100° overnight. The temperature was then increased to 200° for an additional 24 hours. The reaction was then diluted with 500 mL of water and filtered. The solution was then acidified with concentrated hydrochloric acid. A black solid was filtered off and washed with water. The black semisolid was chromatographed on silica gel using methylene chloride:petroleum ether/1:9 to yield a clear oil. The oil was mixed with 30 mL of glacial acetic acid and 5 mL of 30% aqueous hydrogen peroxide and heated on a steam bath overnight. The solution was diluted with water and extracted with 3×100 mL of methylene chloride. The combined organic layers were then concentrated in vacuo (water pump) to yield a thick oil which was recrystallized from ethyl acetate/hexane to yield white solid. The solid was then chromatographed on silica gel using methylene chloride to yield 0.136 gm of 3-fluoro-7-isopropoxyphenoxathiin 10,10-dioxide, m.p. 135–136.5°.

Anal Calcd for ($C_{15}H_{13}FO_4S\cdot0.20\ H_2O$), MW 311.94: C,57,76; H,4.33; S,10.28. Found C,57.80; H,4.20; S,10.16.

Example 10

3-tert-Butoxyphenoxathiin 10,10-dioxide 4-Bromo-3-nitro-tert-butoxybenzene

A mixture of 8.06 gm (36.97 mmol) of 4-bromo-3-nitrophenol (CAS 78137-76-5), 50 mL of methylene chloride, and 15 $\mu$L of 96% sulfuric acid were placed in a flask equipped with a dry ice-acetone condenser, magnetic stirrer, water bath and gas inlet, and stirred. Isobutylene was added through the gas inlet for 2.5 hours. A slight exotherm was observed after 20 minutes. The reaction volume had increased ca 20 mL after isobutylene addition was complete. The reaction was stirred overnight. The reaction contents were then concentrated in vacuo (water pump) to ca 30 mL, washed with 3×75 mL of water and concentrated in vacuo (water pump) to yield 8.39 gm of a mixture of solid and oil. This was then chromatographed on silica gel using methylene chloride:petroleum ether/2:3 to yield 4.90 gm of 4-bromo-3-nitro-tert-butoxybenzene of sufficient purity for further synthetic work.

3-tert-butoxyphenoxathiin

A mixture of 3.98 gm (14.52 mmole) of 4-bromo-3-nitro-tert-butoxybenzene, 1.90 gm (15.05 mmole) of 2-(hydroxy)thiophenol (Fairfield Chemical Co.), 3.54 gm (31.62 mmole) of potassium tert—butoxide, 50 mL of sieve dried N,N-dimethylformamide and ca 50 mg 10 micron copper dust (Alfa) was stirred overnight. The reaction temperature was then raised slowly over 9 days: day 2-50°; day 3-70°; day 6-80°; day 8-85°. The reaction was at 95° on the last day. The reaction was then diluted with 800 mL of water, extracted with 300 mL of methylene chloride, 3×400 mL of chloroform. The organic layers were then combined, washed with 400 mL of water, dried with magnesium sulfate, filtered, and concentrated in vacuo (water pump). The residue was then chromatographed on silcia gel using methylene chloride:petroleum ether/2:3 to yield 1.08 gm of 3-tert-butoxypenoxathiin.

3-tert-Butoxyphenoxathiin 10,10-dioxide

A mixture of 1.05 gm (3.85 mmole) of 3-tert-butoxyphenoxathiin, 3.53 gm (11.5 mmole) of potassium peroxymonosulfate compound [OXONE™] (Dupont), 1.14 gm (14 mmole) of sodium acetate, 20 mL of water, and 20 mL of tert-butanol was stirred overnight. The reaction was diluted with 50 mL of water and extracted with 3×75 mL of chloroform. The combined organic layers were then washed with 2×100 mL of water and concentrated in vacuo (water pump). The residue was then chromatographed on silica gel using methylene chloride to yield 0.89 gm of 3-tert-butoxyphenoxathiin 10,10-dioxide, m.p. 108–110°.

Anal. Calcd for ($C_{16}H_{16}SO_4$), MW=304.38: C,63.13; H,5.31; S,10.53. Found C,63.01; H, 5.34; S, 10.63.

Example 11

(rac)-3-(1-methylpropoxy)phenoxathiin 10,10-dioxide and (R)-3-(1-methylpropoxy)phenoxathiin 10,10-dioxide and (S)-3-(1-methylpropoxy)phenoxathiin 10,10-dioxide.

All were made by the procedure illustrated for the (R) compound:

A mixture of 2.49 g (0.01M) of 3-hydroxyphenoxathiin 10,10-dioxide, (see Example 7) 0.79 g (0.0107M) of (R)-2-butanol, 2.67 g of triphenylphosphine (0.0102 mL) and 25 mL of dried, peroxide-free tetrahydrofuran were shaken to form a solution, then treated with 1.85 g (0.0102M) of diethyl axodicarboxylate. Slight spontaneous warming occurred. The reaction was shaken briefly and allowed to remain at room temperature under $N_2$ for 23 hours. Evaporation of solvent at water aspirator pressure left 7.98 g of a paste, which was warmed with 240 mL of 1 volume of ethyl acetate: 3 volumes of hexanes then cooled and filtered. The filtrate was chromatographed on a 3" diameter by 5" high column of 230–400 mesh silica gel using a mixture of 1 volume of ethyl acetate: 3 volumes of hexanes. Samples of column effluent were checked by TLC (silica gel SK6F plates, 1 volume of ethyl acetate: 3 volumes of hexanes, detection by fluorescence under 254 mμ UV light). Eluents with a spot with Rf around 0.5 (400 mL to 1700 mL) were combined and evaporated down in vacuo. The resulting oil was crystallized from ca. 5% ethyl acetate: 95% hexanes by cooling to −14° giving 1.27 g of white crystals Anal. Calcd by $C_{16}H_{16}O_4S$, MW 304.36: C, 63.14, H,5.30, S, 10.54. Found: For (RS)-product of mp 85.8–88.6°: C,63.08; H,5.31; S,10.60. Found for (S)—compound of m.p. 74.7–76.10°: C, 63.10; H, 5.30; S, 10.60. Found for (R) compound of m.p. 73.3–74.2°: C,63.24; H, 5.31; S, 10.47.

Each of the chiral forms was found to be about 99% of a single chiral isomer containing about 1% of the other isomer on analytical chromatography on a chiral OJ column (Daicel Chemical Industries, Ltd.) using 5% isopropanol: 95% hexanes by volume.

Example 12

General Experimental Conditions for Examples 13 to 36

Reactions requiring anhydrous solvents were performed in flame-dried glassware under a nitrogen atmosphere. Unless otherwise noted, commercially available compounds were used without further purification and purchased from Aldrich. 4-Bromo-3-nitroanisole and 2-hydroxythiophenol were purchased from Lancaster Synthesis Inc. N-Fluorobenzenesulfonimide (NFSi) was purchased from Allied-Signal. 4-Methoxybenzyl disulfide was prepared from the corresponding thiol using a literature procedure (Gordon, E. M. et al. J. Med. Chem. 1988, 31, 2199) Trimethylchlorosilane (TMSCl) was distilled from $CaH_2$ immediately before using. N,N,N',N'-tetramethylethylenediamine (TMEDA) was distilled from $CaH_2$ and stored under nitrogen over 4-Å molecular sieves. Commercial solutions of sec-butyllithium (1.3 M in cyclohexane) were used. Except for tetrahydrofuran (THF), "anhydrous solvents" refers to those purchased from Aldrich in Sure/Seal™ bottles. THF was freshly distilled from potassium before use. Metalations were carried out using standard syringe-septum cap techniques.

Column chromatography was carried out on EM Science silica gel 60 (particle size 230–400 mesh ASTM). Radial chromatography was carried out on 2 mm plates coated with EM Science silica gel 60 containing gypsum using a Chromatotron (model #7924T, Harrison Research) fitted with a solvent pump (model #RPG150-OSSY, Fluid Metering Inc.). Thin-layer chromatography (TLC) was performed with Whatman silica gel 60A TLC plates (250 μm). Analytical high-pressure liquid chromatography (HPLC) was performed on a Vydac C-18 column (0.46×25 cm, 5 μm particle size)) using a Waters 600E pumping system. Peaks were observed with a uv detector set at 220 nm. Solvents used for HPLC elution were as follows: A, 0.1% (v/v) trifluoroacetic acid (TFA) in $H_2O$; B, 0.1% TFA in $CH_3CN$. The column was eluted with a linear gradient of 10–90% of solvent B in A over the course of 15 min at a flow rate of 1.5 mL/min. Retention times ($T_r$) are reported in minutes.

$^1$H-NMR spectra were measured at 200 and 300 MHz with Varian XL spectrometers. Chemical shifts are in parts per million (δ), relative to the observed solvent resonance (eg $CDCl_3$, 7.24). Multiplicities are designated as singlet (s), doublet (d), triplet (t), quartet (q), multiplet (m) and broad (br). $^{19}$F-NMR spectra were measured at 282 MHz on a Varian XL-300 spectrometer and are not referenced.

Example 13

O-Phenoxathiin-3-yl N,N-diethylthiocarbamate

A solution of 3-hydroxyphenoxathiin (310 mg, 1.43 mmol) (Example 7), $Et_3N$ (0.30 ml, 2.15 mmol) and N,N-diethylthiocarbamoyl chloride (238 mg, 1.57 mmol) in EtOAc (25 mL) was refluxed for 3 h, cooled to room temperature and the precipitated hydrochloride salt filtered. The filtrate was washed with 10% aqueous HCl (30 mL), saturated aqueous $NaHCO_3$ (30 mL) and brine (30 mL), dried (Na2SO4), and concentrated in vacuo to an orange oil (479 mg). The crude product was purified by radial chromatography (EtOAc/hexane 10:90) to give 282 mg (66%) of the title compound as a white solid: mp 121–123° (EtOAc); TLC (EtOAc/hexane, 15:85) $R_f$=0.43; $^1$H-NMR ($CDCl_3$) δ 1.32 (=7Hz, 6H), δ 3.68 (q. J=7 Hz, 2 H), δ 3.90 (q, J=7 Hz, 2 H), δ 6.75 (d, J=6 Hz, 1 H, $C_2$-H), δ 6.78 (s, 1 H, $C_4$-H), δ 6.95–7.13 (m, 5H): MS m/e (relative intensity) 332 (MH$^+$, 100), 116 (22).

Anal. Calcd for $C_{17}H_{17}NO_2S_2$: C, 61.60; H, 5.18; N, 4.23 S, 19.34. Found: C, 61.66; H, 5.21; N, 4.20, S, 19.24:

Example 14

O-[4-(Trimethylsilyl)penoxathiin-3-yl] N,N-diethylthiocarbamate

A solution of sec-butyllithium (5.8 ml of a 1.3 M solution in cyclohexane, 7.5 mmol) was added dropwise over 15 min. to a stirred solution of O-phenoxathiin-3-yl N,N-diethylthiocarbamate (2.00 g, 6.03 mmol) (Example 13) and TMEDA (1.14 mL, 7.54 mmol) in 40 mL anhydrous THF at −65° C. (internal bath temperature). The colorless solution was stirred at −60 to −70° C. for 45 min followed by addition of TMSCl (1.15 ml, 9.05 mmol). After stirring at −60° C. for 15 min saturated aqueous $NH_4Cl$ (25 mL) was added and the reaction allowed to warm to ambient temperature. EtOAc (50 mL) and $H_2O$ (25 mL) were added, the organic phase washed with brine (75 mL), dried ($Na_2SO_4$), and concentrated in vacuo to a viscous, yellow oil (2.48 g). Purification by column chromatography ($CH_2Cl_2$/hexane, gradient elution, 10:90 to 40:60) gave 2.04 g (84%) of the title compound as an off-white foam: TLC ($CH_2Cl_2$/hexane, 30:70) $R_f$=0.20; $^1$H-NMR ($CDCl_3$ δ 0.40 (s, 9 H), δ 1.30 (t, J=7 Hz, 6 H), δ 3.79 (m, J=7 Hz, 4 H), δ 6.60 (d, J=8 Hz, 1 H, $C_2$-H), δ 7.01–7.11 (m, 5 H); MS m/e (relative intensity) 404 (MH$^+$, 100), 388 (28), 116 (32).

Anal. Calcd for $C_{20}H_{25}NO_2S_2Si$: C,59.51; H, 6.24; N, 3.47, S, 15.89. Found: C, 59.40; H, 6.20; N, 3.40, S, 15.81.

Example 15

Fluorination of O-[4-(trimethylsilyl)phenoxathiin-3-yl] N,N-diethylthiocarbamate:

O-[1-fluoro-4-(trimethylsilyl)phenoxathiin-3-yl]N, N-diethylthiocarbamate and

O-[1,2-difluoro-4-(trimethylsilyl)penoxathiin-3-yl] N,N-diethylthiocarbamate

A solution of sec-butyllithium (5.17 ml of a 1.2 M solution in cyclohexane, 6.31 mmol) was added dropwise over 1.5 h, to a stirred solution of O-[4-(trimethylsilyl) penoxathiin-3-yl]N,N-diethylthiocarbamate (Example 14)

6, (2.04 g, 5.05 mmol) and TMEDA (0.95 ml, 6.31 mmol) in 30 mL anhydrous THF at −65° C. (internal bath temperature). The pale, yellow solution was stirred at −60° to −70° C. for 1 hr followed by dropwise addition of a solution of NFSi (2.39 g, 7.58 mmol) in anhydrous THF over 2 hr. After stirring at −60° C. for 15 min saturated aqueous NH$_4$Cl (25 mL) was added and the reaction allowed to warm to ambient temperature. EtOAc (50 mL) and H$_2$O (25 mL) were added and the organic phase washed with brine (75 mL), dried (Na$_2$SO$_4$), and concentrated in vacuo to a viscous, yellow oil. (2.48 g). Purification by column chromatography (CH$_2$Cl$_2$/hexane gradient elution, 10:90 to 25:75) eluted 0.30 g (14%) of O-[1,2-difluoro-4-(trimethylsilyl)phenoxathiin-3-yl]N,N-diethylthiocarbamate and 0.45 g (21% of O-[1-fluoro-4-trimethylsilyl)phenoxathiin-yl]N,N-diethylthiocarbamate as yellow solids, followed by 0.82 g (40%) of unreacted O-[4-(trimethylsilyl)phenoxathiin-3-yl] N,N-diethylthiocarbamate).

For O-[1,2-difluoro-4-(trimethylsilyl)phenoxathiin-3-yl], N,N-diethylthiocarbamate: TLC (CH$_2$Cl$_2$/hexane, 20:80) R$_{f=0.15}$; $^1$H-NMR (CDCl$_3$ δ 0.39 (s, 9 H), δ 1.30 (m, 6 H), δ 3.38–4.11 (m, 4 H), δ 6.99–7.18 (m, 4 H); $^{19}$F-NMR (CDCl$_3$) C$_1$- and C$_2$F (d, J=21.5 Hz); MS m/z (relative intensity) 440 (MH$^+$, 100), 424 (44), 116 (30).

Anal. Calcd for C$_{20}$H$_{23}$F$_2$NO$_2$S$_2$Si: C, 54.64; H, 5.27; N, 3.19; S, 14.59. Found: C, 54.76; H, 5.33; N, 3.12; S, 14.49.

For O-[1-fluoro-4-(trimethylsilyl)phenoxathiin-yl] N,N-Diethylthiocarbamate TLC (CH$_2$Cl$_2$/hexane, 20:80) R$_f$=0.10; $^1$H-NMR (CDCl$_3$) δ 0.37 (s, 9 H), δ 1.30 (t, J=7 Hz, 6 H), δ 3.64–3.89 (m, 4 H), δ 6.44 (d, J=9 Hz, 1 H, C$_1$-H), δ 7.00–7.13 (m, 4 H); $^{19}$F-NMR (CDCl$_3$) C$_1$-F (d, J=9 Hz); MS m/e (relative intensity) 422 (MH$^+$, 100), 406 (44), 116 (24).

Anal. Calcd for C$_{20}$H$_{24}$FNO$_2$S$_2$Si: C, 56.97; H, 5.74; N, 3.32; S, 15.21. Found: C, 57.09; H, 5.80; N, 3.26; S, 15.12.

Example 16

O-[1,2-(Difluoro)phenoxathiin-3-yl]N,N-Diethylthiocarbamate

A solution of O-[1,2-difluoro-4-(trimethylsilyl)phenoxathiin-3-yl]N,N-diethylthiocarbamate (300 mg, 0.68 mmol) (Example 15) and CsF (210 mg, 1.36 mmol) in 20 ml 10% (v/v) aqueous DMF was heated under nitrogen at 100° C. for 1.5 h. After cooling to room temperature the reaction was diluted with Et$_2$O (75 mL) and H$_2$O (75 mL). The Et$_2$O layer was washed with brine (75 mL), dried (Na$_2$SO$_4$), and concentrated in vacuo to give 208 mg (84%) O-[1,2-(difluoro)phenoxathiin-3-yl] N,N-diethylthiocarbamate the title compound as a yellow oil which was carried on without further purification: TLC (CH$_2$Cl$_2$/hexane, 50:50) R$_f$=0.49; $^1$H-NMR (CDCl$_3$) δ 1.32 (t, J=7 Hz, 6 H), δ 3.67 (q, J=Hz, 2 H), δ 3.87 (q, J=7 Hz, 2 H), δ 6.64 (dd, J=6 Hz, J=2 Hz, 1 H, C$_4$-H), δ 6.94–7.15 (m, 4 H); $^{19}$F-NMR (CDCl$_3$) C$_1$-F (d, J=21.4 Hz), C$_2$-F (dd, J=21.4 Hz, J=6 Hz).

Example 17

1,2-Difluoro-3-isopropoxyphenoxathiin 10,10-dioxide

A suspension of O-[1,2-difluoro)phenoxathiin-3yl] N,N-diethylthiocarbamate (200 mg, 0.54 mmol) (Example 16) and H$_2$NNH$_2$.H$_2$O (2.64 mL, 54.4 mmol) in 20 mL absolute EtOH was refluxed for 2 h. After cooling, to room temperature the reaction was diluted with EtOAc (75 mL), washed with 10% aqueous HCl (100 mL) and brine (100 mL), dried (Na$_2$SO$_4$), and concentrated in vacuo to 130 mg of crude 1,2-difluoro-3-phenoxathiinol as a yellow-brown solid: TLC (EtOAc/hexane, 40:60) R$_f$=0.46; $^1$H-NMR (CDCl$_3$) δ 6.53 (dd. J=6 Hz, J=2 Hz, 1 H, C$_4$-H), δ 6.97–7.15 (m, 4 H). A mixture of crude 1,2-difluoro-3-phenoxathiinol (110 mg, 0.44 mmol), 2-iodopropane (0.09 ml, 0.87 mmol), Cs$_2$CO$_3$ (0.28 g, 0.87 mmol) and 7 ml anhydrous DMF was stirred under nitrogen at 0° C. for 5 h. The reaction was diluted with Et$_2$O (50 ml) and water (50 ml), the Et$_2$O fraction washed with brine (50 ml), dried (Na$_2$SO$_4$), and concentrated in vacuo to 118 mg of an orange oil. Filtration of the crude product through 10 g of silica gel with 200 ml of EtOAc/hexane (5:95) gave 116 mg (91%) of 1,2-difluoro-3-isopropoxyphenoxathiin as a pale orange oil: TLC (EtOAc/hexane, 20:80) R$_f$=0.58; $^1$H-NMR (CDCl$_3$) δ 1.36 (d, J=6 Hz, 6 H), δ 4.50 (m, J=6 Hz H), δ 6.50 (dd, J=Hz, J=2 Hz, 1 H, C$_4$-H), δ 6.96–7.15 (m, 4 H); $^{19}$F-NMR (CDCl$_3$) C$_1$-F (d, J=21.4 Hz), C$_2$-F (dd, J=21.4 Hz, J=6 Hz). A solution of 1,2-difluoro-3-isopropoxyphenoxathiin (112 mg, 0.38 mmol) and 30% aqueous H$_2$O$_2$ (0.4 ml, 3.8 mmol) in 3 ml glacial AcOH was heated at 80° C. for 2.5 h. After cooling to room temperature the solution was concentrated in vacuo to a white solid. Refrigeration of the crude product in 4 ml of 1:1 EtOAc/hexane overnight afforded 79 mg (44% from O-[1,2-(difluoro)phenoxathiin-3-yl] N,N-diethylthiocarbamate) of the title compound as yellow crystals: mp 174–175° C. (EtOAc/hexane); $^1$H-NMR (DMSO-d$_6$) δ 1.33 (d, J=6 Hz, 6 H), δ 4.94 (m, J=6 Hz, 1 H), δ 7.31 (dd, J=6 Hz, J=2 Hz, 1 H, C$_4$-H), δ 7.30–7.57 (m, 2 H), δ 8.04 (dt, J=7 Hz, J=1 Hz, 1H, C$_8$-H), δ 8.06 (dd, J=8 Hz, J=1 Hz, 1 H, C$_9$-H); $^{19}$F-NMR (DMSO-d$_6$) C$_1$-F (dd, J=21.2 Hz, J=6 Hz); MS m/e (relative intensity) 327 (MH$^+$, 100).

Anal. Calcd for C$_{15}$H$_{12}$F$_2$O$_4$S: C, 55.21; H, 3.71; S, 9.83. Found: C, 55.16; H, 3.71; S, 9.90.

Example 18

0-3-Fluorophenyl N,N-Diethylcarbamate

A solution of 3-fluorophenol (5.00 g, 44.60 mmol), Et$_3$N (9.28 ml, 66.90 mmol), diethylcarbamyl chloride (6.22 ml, 49.06 mmol) and 4-dimethylaminopyridine DMAP (1.09 g, 8.92 mmol) in 100 ml EtOAc was refluxed under nitrogen for 3 h. After cooling, precipitated Et$_3$N HCL was removed by filtration, the yellow filtrate washed with 10% aqueous HCL (100 ml), saturated aqueous NaHCO$_3$ (100 ml) and brine (100 ml), dried (Na$_2$SO$_4$) then concentrated in vacuo to an orange oil (9.33 g). Purification by column chromatography yielded 9.10 g (97%) of the title compound as a yellow liquid: TLC (EtOAc/hexane, 15:85) R$_f$=0.47; MS m/e (relative intensity) 212 (MH$^+$, 100).

Anal. Calcd for C$_{11}$H$_{14}$F$_N$O$_2$: C.62.53; H, 6.69; N,6.63. Found: C,62.64;H,6.73;N,6.68.

Example 19

O-2-(4-Methoxybenzyl)thio)-3-fluorophenyl N,N-Diethylcarbamate

A solution of sec-butyllithium (23.7 ml of a 1.3 M solution in cyclohexane, 30.77 mmol) was added dropwise, over 20 min, to a stirred solution of O-3-fluorophenyl N,N-diethylcarbamate (5.00 g, 23.67 mmol) (Example 18) and TMEDA (4.6 ml, 30.77 mmol) in 50 ml anhydrous THF at −65° C. reaction temperature under N$_2$. The bright yellow solution was stirred at −60 to −70° C. for 1 h followed by dropwise addition of 4-methoxybenzyl disulfide (10.90 g, 35.51 mmol) in 50 ml anhydrous THF. After the reaction had been stirred at −60° C. for 1 h, saturated aqueous NH$_4$Cl (50 ml) was added and the reaction stirred at ambient temperature overnight. Following addition of H$_2$O (100 ml) the reaction mixture was extracted with EtOAc (2×100 ml), the combined organic fractions washed with brine (200 ml), dried (Na$_2$SO$_4$), and concentrated in vacuo to an orange gum (15.67 g). Purification by column chromatography (EtOAc/hexane 10:90) afforded 7.10 g (86%) of the title compound as a yellow oil: TLC (EtOAc/hexane 20:80) R$_f$=0.24; $^1$H-NMR (CDCl$_3$) δ 1.25 (m, 6 H), δ 3.40 (m, 4 H), δ 3.76 (s, 3 H), δ 3.97 (s, 2 H), δ 6.76 (dd, J=Hz, J=2 Hz, 1 H), δ 6.95 (d, J=7 Hz, 1 H), δ 7.13 (dd, J=6 Hz, J=2 Hz, 1H), δ 7.28 (m, 1 H); $^{19}$F-NMR (CDCl$_3$) C$_3$-F(t, J=9 Hz); MS m/e (relative intensity) 364 (MH$^+$, 10), 121 (100), 100 (25).

Anal Calcd for C$_{16}$H$_{18}$O$_2$SSi: C,62.79; H,6.10; N,3.85; S,8.82. Found: C,63.06; H,6.20; N,3.88; S,8.97.

Example 20

3-Fluoro-2-((4-isopropoxy-2-nitrophenyl)thio) phenol and 1-Fluoro-7-isopropoxyphenoxathiin A solution of the O-2-(4-methoxybenzyl)thio)-3-fluorophenyl N,N-diethylcarbamate (4.68 g, 12.88 mmol) and veratrole (3.3 ml, 25.8 mmol) in 14 ml TFA was stirred at ambient temperature under nitrogen for 23 h. The orange reaction was concentrated in vacuo and the oily residue purified by column chromatography (EtOAc/hexane, gradient elution 5:95 to 20:80) affording 900 mg (29% of O-2-thio-3-fluorophenyl N,N-diethy carbamate as a yellow oil which solidified on standing and was stored under nitrogen in a freezer: TLC (EtOAc/hexane 15:85) R$_f$=0.08; HPLC (T$_r$=12.3); $^1$H-NMR (CDCl$_3$) δ 1.15–1.36 (m, 6 H), δ 3.42–3.96 (m, 4 H), δ 6.73 (t, J=8 Hz, 1 H) δ 6.85 (d, J=8 Hz, 1 H), δ 7.16 (br, 1 H, C$_2$-SH), δ 7.29 (m, 1 H).

LiAlH$_4$ (330 mg, 8.6 mmol) was added in three portions over 10 min to a stirred solution of 0-2-thio-3-fluorophenyl N,N-diethylcarbamate (660 mg, 2.7 mmol) in 20 ml anhydrous THF at −20° C. The cooling bath was removed and, after stirring 90 min at room temperature, quenched at −65° C. with 10% aqueous HCl (50 ml). After warming to ambient temperature (1.5 h), the aqueous fraction was extracted with EtOAc (2×75 ml) and the combined organics washed with brine (200 ml), dried (Na$_2$SO$_4$) and concentrated on a rotary evaporator at 35° C. to 395 mg of the unstable 3-fluoro-2-mercaptophenol as a yellow oil: HPLC (T$_r$=11.5); $^1$H-NMR (CDCl$_3$) δ 2.91 (br, 1 H), δ 6.18 (br, 1 H), δ 6.60–6.80 (m, 2 H), δ 7.11–7.22 (m, 1 H).

Potassium tert-butoxide (360 mg, 3.2 mmol) was added to a stirred, degassed, solution of 3-fluoro-2-mercaptophenol (390 mg, 2.7 mmol) and 2-bromo-3-isopropoxynitrobenzene in 20 mL anhydrous DMF and the resulting burgandy-colored reaction heated at 80° C. under N$_2$ overnight (17 h). After cooling to room temperature 10% aqueous HCL (100 ml) was added and the reaction mixture washed with EtOAc (2×75 ml). The combined organics were rinsed with water (2×200 ml), and brine (200 ml), dried (Na$_2$SO$_4$), and concentrated in vacuo to a viscous orange-brown oil. Purification by column chromatography afforded 390 mg (45% from O-2-(4-methoxybenzyl)thio-3-fluorophenyl N,N-diethylcarbamate) of 3-fluoro-2-((4-isopropoxy-2-nitrophenyl)thio)phenol as a yellow solid along with 60 mg (8%) of 1-fluoro-7-isopropoxyphenoxathiin.

For 3-fluoro-2-((4-isopropoxy-2-nitrophenyl)thio)phenol: TLC (EtOAc/hexane 15:85) R$_f$=0.17; HPLC (T$_r$=15.9);

$^1$H-NMR (CDCl$_3$) δ 1.35 (d, J=6 Hz, 6 H), δ 6.60 (br, 1 H, —OH), δ 6.69 (d, J=9 Hz, 1 H), δ 6.81 (t, J=8 Hz, 1 H), δ 6.96 (m, m/e (relative intensity) 324 (MH$^+$, 60), 306 (42), 212 (100).

Anal. Calcd for C$_{15}$H$_{14}$FNO$_4$S: C, 55.72; H, 4.36; N, 4.33; S, 9.92. Found: C, 55.78; H, 4.44; N, 4.27; S, 9.91.

For 1-fluoro-7-isopropoxyphenoxathiin: TLC (CH$_2$Cl$_2$/hexane 10:90) R$_f$=0.23; HPLC (T$_r$=19.3); $^1$H-NMR (CDCl$_3$) δ 1.32 (d, J=6 Hz, 6 H), δ 6.58–7.08 (m, 6 H); MS m/e (relative intensity) 277 (MH$^+$, 100), 235 (16).

Example 21

3-Fluoro-2-((4-isopropoxy-2-nitrophenyl)sulfonyl) phenol

A solution of 3-fluoro-2-((4-isopropoxy-2-nitrophenyl)thio)phenol (367 mg, 1.1 mmol) (Example 20) and CH$_3$CO$_3$H (32% in AcOH, 1.4 ml, 6.6 mmol) in 20 mL glacial AcOH was heated at 50° C. for 5 h. After cooling, the reaction was concentrated in vacuo to an orange-brown solid and purified by radial chromatography (EtOAc/hexane, gradient elution 10:90 to 50:50) to afford 395 mg (100% of the title compound as an orange solid: mp 117–119° C.; TLC (EtOAc/hexane 30:70) R$_f$=0.34; HPLC (T$_r$=15.4); $^1$H-NMR (CDCl$_3$) δ1.32 (d, J=6 Hz, 6 H), δ 4.85 (m, J=6 Hz, 1 H), δ 6.73–6.86 (m, 2 H), δ 7.41–7.56 (m, 3 H), δ 8.20 (d, J=9 Hz), 1 H), δ 11.25 (s, 1 H, —OH); MS m/e (relative intensity) 356 (MH$^+$, 60), 244 (97).

Anal. Calcd for C$_{15}$H$_{14}$FNO$_6$S: C, 50.70; H, 3.97; N, 3.94; S, 9.02. Found: C, 50.80; H, 3.95; N, 3.89;

Example 22

1-Fluoro-7-isopropoxyphenoxathiin 10,10-dioxide [9-Fluoro-3-isopropoxyphenoxathiin 10,10-dioxide]

From 1-fluoro-7-isopropoxyphenoxathiin (Example 20): A stirred solution of 1-fluoro-7-isopropoxyphenoxathiin (50 mg, 0.18 mmol) and 30% aqueous H$_2$O$_2$ (0.2 mL, 1.8 mmol) in 3 mL glacial acetic acid was heated at 80° C. for 4 h. After cooling, the solution concentrated in vacuo to a brown solid purified by preparative TLC (EtOAc/hexane 25.75) to give a white solid. Crystallization from EtOAc/hexane (1:4) afforded 35 mg (61%) of the title compound: mp 151–152° C. (EtOAc/hexane); TLC (EtOAc/hexane 15:85) R$_f$=0.34; HPLC (T$_r$=15.1); $^1$H-NMR (DMSO-d$_6$) δ 1.32 (d, J=6 Hz, 6 H), δ 4.86 (m, J=6 Hz, 1 H), δ 7.09 (dd, J=7 Hz, J=2 Hz, 1 H, C$_2$—H), δ 7.11 (s, 1 H, C$_4$—H), δ 7.36–7.46 (m, 2 H), δ 7.85 (m, 1 H, C$_8$—H), δ 7.98 (d, J=9.5 Hz, 1 H, C$_1$—H; MS m/e (relative intensity) 309 (MH$^+$, 100).

Anal. Calcd. for C$_{15}$H$_{13}$FO$_4$S: C, 58.43; H, 4.25; S, 10.40. Found: C, 58.36; H, 4.25; S, 10.30.

From 3-fluoro-2-((4-isopropoxy-2-nitrophenyl) sulphonyl)phenol (Example 21): A stirred solution of 3-fluoro-2-((4-isopropoxy-2-nitrophenyl))sulphonyl)phenol (0.35 g, 0.98 mmol) and potassium tert-butoxide (0.13 g, 1.18 mmol) in 25 mL anhydrous DMF was heated at 80° C. for 1 h during which time the reaction color changed from orange to light yellow. After the reaction had been cooled 10% aqueous HCL (100 mL) was added and the mixture extracted with EtOAc (2×100 mL). The combined organics were washed with 10% aqueous HCl (100 mL) and brine (100 mL), dried (Na$_2$SO$_4$) and concentrated in vacuo to a yellow solid (290 mg). Recrystallization from etOAC/hexane gave 210 mg (70%) of the title compound which was identical in all aspects to material prepared from 1-Fluoro-7-isopropoxyphenoxathiin (Example 20).

Anal. Calcd for $C_{15}H_{13}FO_4S$: C, 58.43; H, 4.25; S, 10.40. Found: C, 58.24; H, 4.28; S, 10.23.

Example 23

3-Isopropoxyphenoxathiin

To a stirred suspension of potassium tert-butoxide (2.02 g, 18.02 mmol) in 25 ml anhydrous DMF was added, dropwise, 2-hydroxy-4isopropoxy-2'-nitrodiphenylsulfide (Example 4) in 15 mL DMF over 20 min under nitrogen. The resulting dark brown mixture was heated at 150° C. for 48 h, the solvent removed in vacuo at 40° C. (1.0 mm), and the brown, oily residue purified by column chromatography ($CH_2Cl_2$/hexane, gradient elution, 5:95 to 40:60) to yield 2.94 g (70%) of the title compound as a yellow oil: TLC (EtOAc/hexane 2.98) $R_f$=0.28; HPLC ($T_r$=20.0); $^1$H-NMR ($CDCl_3$) δ 1.32 (d, J=6 Hz, 6 H), δ 4.49 (m, J=6 Hz, 1 H), δ 6.57–6.62 (m, 2 H, $C_2$— and $C_{4-H}$), δ 6.95–7.15 (m, 5 H), MS m/z (relative intensity) 259 (MH+, 100), 217 (28).

Example 24

3-Isopropoxy-(4-trimethylsily)phenoxathiin

A solution of sec-butyllithium (8.30 ml of a 0.8 M solution in cyclohexane, 6.60 mL) was added dropwise, over 5 min, to a stirred solution of 3-isopropoxyphenoxathiin (1.42 g. 5.50 mmol) (Example 23) and TMEDA (1.00 mL, 6.60 mmol) in 20 ml anhydrous THF at −70° C. (internal bath temperature). The solution was stirred at −60 to −70° C. for 30 min followed by addition of TMSCl (0.90 mL, 8.25 mmol). After stirring at −60° C. for 45 min, the reaction was quenched by adding 50 ml saturated aqueous $NH_4Cl$. The reaction was allowed to warm to room temperature over 1.5 h. The crude organic product was extracted with EtOAc (2×50 mL). The combined EtOAc layers were washed with brine (100 mL), dried over $Na_2SO_4$, and concentrated in vacuo to a golden oil (1.79 g). Purification by column chromatography (petroleum ether) afforded 1.30 g (72%) of the title compound as a pale yellow oil: TLC (hexane) $R_f$=0.32; $^1$H-NMR ($CDCl_3$) d 0.42 (s, 9H), d 1.32 (d, J=6 Hz, 6 H), d 4.49–4.61 (m, 1 H), d 6.52 (d, J=8 Hz, 1 H, $C_2$—H), d 6.96–7.26 (m, 5 H), MS m/e (relative intensity) 330 (M+, 100), 315 (94).

Anal. Calcd. for $C_{18}H_{22}O_2SSi$: C, 65.41; H, 6.71; S, 9.70. Found: C, 65.30; H, 6.68; S, 9.79.

Example 25

1-Fluoro-3-isoproxy-4-(trimethylsilyl)phenoxathiin

A solution of sec-butyllithium (5.90 mL of a 0.8 M solution in cyclohexane, 4.72 mmol) was added dropwise, over 15 min, to a stirred solution of 3-isopropoxy-(4-trimethylsilyl)phenoxathiin (1.25 g, 3.78 mmol) (Example 24) and TMEDA (0.71 ml, 4.72 mmol) in 20 mL anhydrous THF at −70° C. (internal bath temperature). The pale yellow solution was stirred at −60–70° C. for 1 h followed by dropwise addition of N-fluorobenzensulfonimide (1.79 g, 5.67 mmol) in 15 mL anhydrous THF. After 45 min, saturated aqueous $NH_4Cl$ (30 mL) were added. The resulting heterogeneous mixture was stirred at ambient temperature for 30 min. EtOAc (25 mL) and $H_2O$ (25 mL) was added, the organic layer washed with brine (30 mL), dried ($Na_2SO_4$), and concentrated in vacuo to a yellow gum (1.12 g). Purification by flash column chromatography (hexane) afforded 412 mg (31%) of the title compound as a colorless oil. Further elution yielded 351 mg (28%) of unreacted 3-isoproproxy-(4-trimethyl-silyl)phenoxathiin. For the title compound: TLC (hexane) showed 1 spot, $R_f$= 0.29; $^1$H NMR ($CDCl_3$), (d, J=6.1 Hz, 6 H), d 4.42–4.48 (m, 1 H), d 6.34 (d, J=11.3 Hz, 1 H, $C_2$—H), d 6.98–7.12 (m, 4 H); MS m/e (relative intensity) 348 (M+, 100), 333 (85).

Anal Calcd. for $C_{16}H_{18}O_2SSi$: C, 62.04; H, 6.07; S, 9.20. Found: C, 61.98; H, 6.04; S, 9.11.

Example 26

1-Fluoro-3-isopropoxyphenoxathiin

A stirred solution of 1-fluoro-3-isopropoxy-4-(trimethylsilyl)phenoxathiin (230 mg, 0.66 mmol) (Example 25) and CsF (200 mg, 1.32 mmol) in 5 mL 10% (v/v) aqueous DMF was heated under nitrogen at 100° C. for 0.5 h. After cooling to room temperature, the reaction was diluted with brine (30 mL), dried ($Na_2SO_4$), and concentrated in vacuo to a pale yellow oil (178 mg). Filtration of the crude product through silica gel (20 g) with 10% $CH_2Cl_2$/hexanes yielded 142 mg (78%) of the title compound as a colorless oil: TLC ($CH_2Cl_2$/hexanes, 10:90) $R_f$=0.31; $^1$H-NMR ($CDCl_3$) d, J=6 Hz, 6 H), 4.43–4.47 (m, 1 H), d 6.36–6.41 (m, 2 H), $C_2$—H and $C_4$-H), d 6.95–7.14 (m, 4 H); MS m/e (relative intensity) 277 (MH+, 100).

Anal. Calc for $C_{15}H_{13}FO_2S$: C, 65.20; H, 4.74; S, 11.60. Found: C, 65.31; H, 4.74; S, 11.69.

Example 27

1-Fluoro-3-isopropoxyphenoxathiin 10,10-dioxide

A solution of 1-fluoro-3-isopropoxyphenoxathiin (117 mg, 0.42 mmol) (Example 26) and 30% aqueous $H_2O_2$ (0.48 g, 4.23 mmol) in 10 mL glacial acetic acid was stirred at room temperature for 0.5 h and then heated at 90° C. for 90 min. After cooling to room temperature, a white solid crystallized and water (50 mL) was added to complete precipitation. The crude product was filtered, washed with water (10 mL) and purified by radial chromatography with 30% $CH_2Cl_2$/hexane, 1:1) $R_f$=0.13; $^1$H-NMR ($CDCl_3$ d 1.39 (d, J=6.1 Hz, 6 H), d 4.56–4.64 (m, 1 H), d 6.62–6.6 (m, 2 H, $C_2$— and $C_4$—H), d 7.25–7.42 (m, 2 H), d 7.59–7.65 (m, 1 H), d 8.05 (dt, J=8 Hz, J=1.5 Hz, 1 H, $C_9$—H); MS m/e (relative intensity) 309 (M+, 100).

Anal. Calcd for $C_{15}H_{13}FO_4S$: C, 58.23; H, 4.23; S, 10.40. Found: C, 58.32; H, 4.21; S, 10.30.

Example 28

5-Fluoro-6-hydroxy-2,3-benzoxathio-2-one

A mixture of 6hydroxy-1,3-benzoxathio-2-one (1.51 g, 8.98 mmol) and 1,2-dichloroethane (90 mL) was heated to 60° C. and 3,5-dichloro-1-fluoropyridinium triflate (4.98 g, 15.76 mmol) was added in ca. 1 g portions over a 30 min period. The reaction mixture was heated to reflux and maintained for 20 min and then allowed to cool to rt. The mixture was diluted with EtOAc to dissolve the isoluble material and the crude product absorbed onto silica gel. Flash chromatography on silica gel eluting with $CH_2Cl_2$ provided the product 5-fluoro-6hydroxy-1,3-benzoxathiol-2-one (0.470 g, 2.52 mmol, 28% yield) as an off white solid, m.p. 141–143° C., ca. 7% of this material was present as the 7-fluoro isomer.

Anal. Calcd for $C_7H_3FO_3S$: C, 45.16; H, 1.62; S, 17.22. Found: C, 45.17; H, 1.67; S, 17.13.

Example 29

6-Isopropoxy-1,3-benzoxathiol-2-ones

In a typical procedure, anhydrous $K_2CO_3$ (8 mmol) was added to a solution of the 6-hydroxy-1,3-benzoxathiolone (4 mmol) and isopropyl iodide (14 mmol) in DMF (18 mL) and the mixture stirred at rt for 3.5 h. The DMF was removed by rotovap and the crude material was dissolved in Et$_2$O (50 ml). The Et$_2$O layer was washed with H$_2$O (3×10 mL), dried over MgSO$_4$, filtered and concentrated. Flash chromatography on silica gel eluting with 6–7.5% EtOAc/hexanes provided the product.

(a) 6-Isopropoxy-1,3-benzoxathio-2-one: from 6-hydroxy-1,3-benzoxathiol-2-one; colorless oil; 88% yield. Anal. Calcd for C$_{10}$H$_{10}$O$_3$S: C, 57.13; H, 4.79; S, 15.25. Found C, 57.25; H, 4.75; S, 15.18.

(b) 5Fluoro-6-isopropoxy-1,3-benzoxathiol-2-one from 5-fluoro-6-hydroxy-1,3-benzoxathiol-2-one (see Example 28); white solid; 67% yield; mp 52–54° C.; Anal. Calcd for C$_{10}$H$_9$FO$_3$S: C, 52.62; H, 3.97; S, 14.04. Found: C, 52.69; H, 3.96; S, 14.13.

Example 30

2-Hydroxythiophenols

A solution of KOH (4 mmol) in (1 mL) and MeOH (0.5 mL) was added to a stirring solution of the isopropoxybenzoxathiolone (see Example 29) (1.5 mmol) in MeOH (3 ml). The resulting solution was stirred 10 min at room temperature and acidified with conc. HCl to ca. pH 1. The MeOH was removed at reduced pressure and the aqueous mixture extracted with EtOAc (2.×25 ml). The EtOAc layers were dried over MgSO$_4$, filtered and concentrated to provide the product which was used immediately without further purification.

(a) 2-Hydroxy-4-isopropoxythiophenol: from 6-isopropoxy-1,3-benzoxathiol-2-one; light yellow oil; 100% crude yield.

(b) 5-Fluoro-2-hydroxy-4-isopropoxythiophenol: from 5-fluoro-6-isopropoxy-1,3-benzoxathiol-2-one; light yellow oil; 100% crude yield.

Example 31

Phenoxathiins: A solution of the 2-hydroxythiophenol (see Example 30) (1.5 mmol) in DMF (3 mL) was added dropwise to a stirring mixture of potassium tert-butoxide (3 mmol) in DMF (2 mL) cooled to 0° C. The resulting mixture was stirred 15 min at ice-bath temperature and a solution of the 1-halo-2-nitrobenzene (1 eq) or tetrafluorobenzene (1–5 eqs) in DMF (3.5 mL) was added dropwise. The reaction mixture was allowed to warm to rt and then heated to reflux for 1–18 h monitoring the reaction by HPLC. When the reaction was judged complete, the mixture was allowed to cool to rt and the DMF was removed by rotovap. The crude product was dissolved in EtOAc and the mixture subjected to a standard aqueous workup followed by flash chromatography on silica gel eluting with EtOAc/Hexanes.

(a) 2-fluoro-3-isopropoxyphenoxathiin: from 5-fluoro-2-hydroxy-4-isopropoxythiophenol; (see Example 30b) and 2-fluoro-nitrobenzene; colorless oil; 39% yield;

Anal. Calcd for C$_{15}$H$_{13}$FO$_2$S: C, 65.20; H, 4.74; S, 11.60. Found: C, 65.18; H, 4.77; S, 11.51.

(b) 2,7-difluoro-3-isopropoxyphenoxathiin from 5-fluoro-2-hydroxy-4-isopropoxythiophenol and 2,5-difluoro nitrobenzene; white solid; 25% yield; mp 102–105° C.;

Anal. Calcd for C$_{15}$H$_{12}$F$_2$O$_2$S: C, 61.21; H, 4.11; S, 10.89. Found: C, 61.11; H, 4.10; S, 10.80.

(c) 7,8-difluoro-3-isopropoxyphenoxathiin: from 2-hydroxy-4-isopropoxythiophenol and 2,5-difluoro nitrobenzene; white solid; 25% yield; mp 102–105° C.;

Anal. Calcd for C$_{15}$H$_{12}$F$_2$O$_2$S: C, 61.21; H, 4.11; S, 10.89. Found: C, 61.11; H, 4.10; S, 10.80.

Example 32

Phenoxathiin10,10-dioxides

In a typical procedure, a solution of the phenoxathiin (see Example 31) (0.5 mmol) in trifluoroacetic acid (2 mL) was cooled to 0° C. and 30% H$_2$O$_2$ (0.3 mL) was added dropwise. The reaction mixture was stirred at ice-bath temperature for 15 min and then at room temperature for an additional 4.5 h. The trifluoroacetic acid was removed at reduce pressure and the crude solid partitioned between CH$_2$Cl$_2$ and sat. NaHCO$_3$. The layers were separated and the aqueous layer extracted with CH$_2$Cl$_2$. The combined organic layers were dried over MgSO$_4$, filtered and concentrated. The product was purified by flash chromatography on silica gel eluting with CH$_2$Cl$_2$/hexanes or by recrystallization from EtOAc/hexanes.

(a) 2-fluoro-3-isopropoxyphenoxathiin10,10-dioxide from 2-fluoro-3-isopropoxyphenoxathiin (see Example 31a) white solid; 72% yield; mp 166–167° C.;

Anal. Calcd for C$_{15}$H$_{13}$FO$_4$S: C, 58.43; H, 4.25; S, 10.40. Found: C, 58.33; H, 4.23; S, 10.35.

(b) 2,7-difluoro-3-isopropoxyphenoxathiin-10,10 dioxide from 2,7-difluoro-3-isopropoxyphenoxathiin (see Example 31b) white solid; 89% yield; mp 162–164° C.;

Anal. Calcd for C$_{15}$H$_{12}$F$_2$O$_4$S: C, 55.21; H, 3.71; S, 9.82. Found: C, 55.11; H, 3.73; S, 9.74.

(c) 7,8-difluoro-3-isopropoxyphenoxathiin10,10-dioxide: from 7,8-difluoro-3-isopropoxyphen-oxathiin (see Example 31c) white solid; 46% yield; mp 144–146° C.;

Anal. Calcd for C$_{15}$H$_{12}$F$_2$O$_4$S: C, 55.21; H, 3.71; S, 9.82. Found: C, 55.29; H, 3.65; S, 9.88.

Example 33

3-Methoxyphenoxathiin 10,10-dioxide was made by oxidation by hot aqueous hydrogen peroxide in acetic acid of 3-methoxyphenoxathiin. The phenoxathiin was made by cyclizing 2-hydroxythiophenol and 2-bromo-5-methoxynitrobenzene with base; m.p. 160–161° C.;

Anal. Calcd; C, 59.53; H, 3.84; S, 12.22. Found: C, 59.40; H, 3.87; S, 12.31.

Example 34

3-Ethoxyphenoxathiin 10,10-dioxide was made by analogous oxidation of 3-ethoxyphenoxathiin. That was made by first demethylation of above 3-methoxyphenoxathiin by heating under reflux with 30–32% HBr in acetic acid and then refluxing the resulting 3-hydroxyphenoxathiin in acetone with ethyl iodide and anhydrous potassium carbonate; mp. 150–151.5° C.;

Anal. calcd.; C, 60.86; H, 4.38; S, 11.60. Found: C, 60.79; H, 4.40; S, 11.65.

Example 35

3-Propoxyphenoxathiin 10,10-dioxide was made similarly oxidizing the reaction product of propyl iodide with 3-hydroxyphenoxathiin m.p. 118–120° C. (recrystallized from CHCl$_3$-Hexane).

Anal. calcd for C$_{15}$H$_{14}$O$_4$S, MW 290.33; C, 62.05; H, 4.86; S, 11.04. Found: C, 61.92; H, 4.88; S, 10.95.

Example 36

3-(pentyloxy)phenoxathiin 10,10-dioxide was made by heating under reflux 3-hydroxyphenoxathiin 10,10-dioxide (made by demethylating 3-methoxyphenoxathiin 10,10-dioxide with HBr in HOAc) with 1-iodopentane and excess anhydrous potassium carbonate in refluxing acetone, m.p. 77–79° (recrystallized from hexane).

Anal. Calcd. For $C_{17}H_{18}O_4S$, MW 318.39: C, 64.13; H, 5.70; S, 10.07. Found: C, 64.02; H, 5.74; S, 10.02.

Example 36a 3-butoxyphenoxathiin 10,10-dioxide was made analogously to Example 36 but using 1-iodobutane, m.p. 105–107° C.

Anal. Calcd. For $C_{16}H_{16}SO_4$: C, 63.13; H, 5.31; S, 10.53. Found: C, 63.07; H, 5.35; S, 10.44.

Example 37

(rac)-2-(3-phenoxathiinyl)propanol S,S-dioxide

This was prepared from 3-hydroxyphenoxathiin 10,10-dioxide by (a) reaction of the potassium salt of that with ethyl 2-bromopropionate;

(b) saponification of the resulting ester and acidification of the salt so produced to give the acid;

(c) reduction of the acid with borane ("diborane") to give the desired propanol.

This generally followed a procedure published by Harfenist and Thorn, J. Org. Chem. (1971) 36, 1171.

(a) (rac)-Ethyl 2-(3-Phenoxathiinyloxy)propionate-S,S-dioxide

A mixture of 6.1 g (0.0246 mole) of 3-hydroxyphenoxathiin 10,10-dioxide, 150 mL of commercial absolute ethanol and 3.30 g of potassium tert-butoxide (nominally 0.029 mole) was stirred under nitrogen until nearly homogeneous. Ethyl 2-bromopropionate, 5.79 g (0.032 mol) was added, and the reaction was heated under reflux with stirring for 19 h., protected by a drying tube with NaOH pellets. The resulting solution was then filtered from ethanol-insoluble solid which was rinsed with water. The water-insoluble residue was combined with the solid remaining after distillation of the ethanol from the initial filtrate and recrystallized twice, from boiling ethanol by addition of water, yielding 3.9 g of white solid m.p. 123.2–125.6, giving a single TLC spot with Rf=0.31 under conditions where the phenol starting material had Rf 0.19 (solvent 1 EtOAc: 3 hexanes, silica gel with fluorescent indicator visualized at 254 nm). Starting phenol was recovered from the mother liquors.

Anal. Calcd. For $C_{17}H_{16}SO_6$, MW 348.37: C, 58.61; H, 4.63; S, 9.20. Found: C, 58.48; H, 4.65; S, 9.09.

Note: Alternative bases to KO— tert—Bu can also be used. Anhydrous bases are preferred. Probably anhydrous potassium carbonate and acetone as solvent would be satisfactory.

(b) (rac)-3-(2-Phenoxathiinyloxy)propionic acid S,S-dioxide

The above ester, 3.9 g was saponified by stirring and heating under reflux for 3.5 h with 1.3 g of KOH pellets labelled 'minimum 87.8%', and 150 mL of ethanol, protected by a NaOH tube. The resulting solution was evaporated to half its volume, several volumes of water was added, and the filtered solution was acidified with HCl. The precipitated white solid was recrystallized from isopropyl alcohol be addition of water near the bp, and cooling. A first crop of 1.84 g mp 215.4 was obtained.

Anal. Calcd. For $C_{15}H_{12}O_6S$, MW 320.32: C, 56.24;; H, 3.78; S, 10.01. Found: C, 56.15; H, 3.72; S, 10.08.

(c) (rac)-2-(3-Phenoxathiinyloxy)propanol S,S-dioxide

To a mixture of 3.08 g (0.0096 mole) of the carboxylic acid prepared under "(b)" and 115 mL of dry, peroxide-free tetrahydropyran (THF) was added dropwise with stirring 110 mL (excess) of 1 molar borane in THF, protecting the reaction with a $N_2$ bubbler system to allow gas evolution. The reaction was allowed to remain overnight, and then the clear solution was treated dropwise with 100 mL of water (gas evolved initially; extreme caution is advised in addition of the first 20 mL). The solution was then concentrated to ca. 100 mL, and 800 mL of water was added to dissolve a white solid, leaving an oil behind. This was dried in ether solution, and chromatographed on silica gel. Solvent removal in vacuo left a sticky glass which gave a single spot on TLC, and had the correct elemental analysis.

Anal. Calcd for $C_{15}H_{14}O_5S$, MW 306.33: C, 58.81; H, 4.61; S, 10.47. Found: C, 58.91; H, 4.57; S, 10.54.

Example 38

6-Isopropoxy-2,2-dimethyl-1,3-benzoxathiazole

A solution of 3-isopropoxy-6-mercaptophenol (1.00 g, 5.43 mmol), acetone (0.95 g, 16.29 mmol) and para-toluenesulfonic acid monohydrate (0.11 g, 0.58 mmol) in 25 mL benzene was refluxed in a 100 ml round bottom flask fitted with a Dean-Stark trap for 1 h. After the reaction had been cooled to room temperature, it was diluted with EtOAc (50 mL), washed with saturated aqueous $NaHCO_3$ (50 mL and brine (50 mL), dried ($Na_2SO_4$), and concentrated in vacuo to a pale, yellow liquid (1.27 g). The crude product was purified by column chromatography (EtOAc/hexane 5:95) to yield 1.15 g (94%) of the title compound as a colorless liquid: TLC (EtOAc/hexane 15:85) $R_f$=0.57; HPLC ($T_r$=15.5); $^1$H-NMR ($CDCl_3$) d 1.30 (d, J=6 Hz, 6 H), d 1.83 (s, 6 H), d 4.43 (m, 1 H), d 6.41 (s, 1 H), d 6.42 (d, J=9 Hz, 1 H), d 6.95 (d, J=9 Hz, 1 H); MS m/z (relative intensity) 225 ($MH^+$, 100), 183 (66).

Anal. Calcd for $C_{12}H_{16}O_2S$: C, 64.22; H, 7.21; S, 14.30. Found: C, 64.35; H, 7.16; S, 14.39.

Example 39

6-Isopropoxy-2,2-dimethyl-7-(trimethylsilyl)-1,3-benzoxathiazole

A solution of sec-butyllithium (8.6 mL of a 1.3 M solution in cyclohexane, 11.15 mmol) was added dropwise, over 10 min, to a stirred solution of 6-isopropoxy-2-2-dimethyl-1,3-benzoxathiazole (2.00 g, 8.92 mmol) (Example 38), and TMEDA (1.68 mL, 11.15 mmol) in 40 mL anhydrous THF at −70° C. (reaction temperature). The solution was stirred at −60–70° C. for 30 min followed by addition of TMSCl (1.70 mL, 13.28 mmol). The cooling bath is removed and the temperature allowed to warm to 15° C. Saturated aqueous warm to ambient temperature. EtOAc (100 mL) was added and the organic phase washed with brine (100 mL), dried ($Na_2SO_4$), and concentrated in vacuo to a pale, yellow oil (2.31 g). The crude product was purified by column chromatography (hexane) to yield 1.80 g (68%) of the title compound as a colorless liquid: TLC (hexane) $R_f$=0.27; $^1$H-NMR ($CDCl_3$) d 0.29 (s, 6 H), d 1.32 (d, J=6 Hz, 6 H), d 1.80 (s, 6 H), d 4.51 (m, 1 H), d 6.33 (d, J=8 Hz, 1 H), d 6.98 (d, J=8 Hz, 1 H); MS m/z (relative intensity) 297 ($MH^+$, 81), 281 (100).

Anal. Calcd for $C_{15}H_{24}O_2SSi$: C, 60.73; H, 8.18; S, 10.82. Found: C, 60.78; H, 8.21; S, 10.92.

Example 40

4-Fluoro-6-isopropoxy-2,2-dimethyl-7-(trimethylsilyl)-1,3-benzoxathiazole

A solution of sec-butyllithium (2.28 mL of a 1.3 M solution in cyclohexane, 2.96 mmol) was added dropwise, over 5 min, to a stirred solution of 6-isopropoxy-2,2-dimethyl-7-(trimethylsilyl)-1,3-benzoxathiazole (0.50 g, 1.69 mmol) (Example 39) and TMEDA (0.44 ml, 2.96 mmol) in 10 mL cyclohexane at 0° C. (reaction temperature). The pale yellow solution was stirred at 0–5° C. for 3 h followed by dropwise addition of N-fluorobenzenesulfonimide (1.06 g, 3.38 mmol) in 5 mL anhydrous THF. After 20 min, saturated aqueous $NH_4Cl$ (25 mL) was added. The resulting heterogeneous mixture was diluted with EtOAc (50 mL) and $H_2O$ (50 mL), the organic layer washed with brine (30 mL), dried ($Na_2SO_4$), and concentrated in vacuo to a yellow-brown oil. The crude oil was triturated with hexane (100 mL), filtered and concentrated to a yellow oil. Purification by flash column chromatography (hexane) afforded 170 mg (32%) of the title compound as a colorless oil. Further elution yielded 250 mg (50%) of unreacted 6-isopropoxy-2,2-dimethyl-7-(trimethylsilyl)-1,3-benzoxathiazole. For the title compound: TLC (hexane) $R_f$=0.34; $^1$H-NMR ($CDCl_3$) d 0.27 (s, 9 H), d 1.32 (d, J=6 Hz, 6 H), d 1.81 (s, 6 H), d 4.44 (m, 1 H), d 6.15 (d, J=11.3 Hz, 1 H, $C_2$—H); $^{19}$F-NMR ($CDCl_3$) $C_1$—F (d, J=11 Hz); MS m/z (relative intensity) 315 (MH$^-$, 100), 299 (86).

Anal. Calcd. for $C_{15}H_{23}FO_2SSi$: C, 57.26; H, 7.39; S, 10.20. Found: C, 57.36; H, 7.44; S, 10.27.

Example 41

4-Fluoro-6-isopropoxy-2,2-dimethyl-1,3-benzoxathiazole

A stirred solution of 4-fluoro-6-isopropoxy-2,2-dimethyl-7-(trimethylsilyl)-1,3-benzoxathiazole (0.64 g, 2.02 mmol) (Example 40) and CsF (0.62 g, 4.04mmol) in 22 ml 10% (v/v) aqueous DMF was heated under nitrogen at 120° C. for 2.5 h. After the reaction had been cooled to room temperature, it was diluted with $Et_2O$ (50 mL) and $H_2O$ (50 mL). The $Et_2O$ layer was washed with brine (50 mL), dried ($Na_2SO_4$), and concentrated in vacuo to a pale yellow oil (525 mg). Purification by column chromatography (EtOAc/hexane, gradient elution, 0:100 to 5:95) yielded 451 mg (92%) of the title compound as a pale, yellow oil: TLC (hexane) $R_f$=0.08; HPLC ($T_r$=15.5); $^1$H NMR ($CDCl_3$) d 1.30 (d, J=6 Hz, 6 H), d 1.84 (s, 6 H), d 4.40 (m, 1 H), d 6.24 (b, 2 H); $^{19}$F-NMR ($CDCl_3$) $C_1$—F (d, J=12 Hz); MS m/z (relative intensity) 243 (MH$^+$, 100), 201 (28).

Anal. Calcd. for $C_{12}H_{15}FO_2S$: C, 59.45; H, 6.25; S, 13.24. Found: C, 59.58; H, 6.32; S, 13.15.

Example 42

3-Fluoro-5-isopropoxy-2-mercaptophenol

A solution of $Hg(CF_3CO_2)_2$ (0.76 g, 1.77 mmol) in $H_2O$ (4 mL) was added dropwise over 1 min to a stirred, reddish, solution of 4-fluoro-6-isopropoxy-2-2-dimethyl-1,3-benzoxathiazole (0.41 g, 1.69 mmol) (Example 41) in TFA (4 mL) at ambient temperature. An orange solid precipitated instantly and, after stirring an additional 10 min, was filtered. The filtered solid was rinsed with $H_2O$ (50 mL) and hexane (30 mL) and then dissolved in 100 mL of 30% (v/v) MeOH/$CH_2Cl_2$. The resulting solution was concentrated in vacuo to yield 0.79 g (91%) of crude (2-fluoro-6-hydroxy-4-isopropoxyphenyl)thio)mercurio 2,2,2-trifluoroacetate as an orange solid which gave a single peak ($T_r$=14.6) by HPLC. A stream of $H_2S$ gas was bubbled through a solution of the mercury adduct (0.76 g, 1.46 mmol) in 25 ml MeOH for 15 min. The precipitated HgS is filtered through a celite pad and rinsed with ether (30 mL). The filtrate was concentrated in vacuo to yield 0.30 g (100%) of the unstable 3-fluoro-5-isopropoxy-2-mercaptophenol as a pale, yellow oil: TLC (EtOAc/hexane 15:85) HPLC ($T_r$=11.6); $^1$H NMR ($CDCl_3$) d 1.31 (d, J=6 Hz, 6 H), d 2.58 (s, 1 H, —O$\underline{H}$), d 4.48 (m, 1 H), d 6.27 (dd, J=2 Hz, J=11 Hz, 1 H, $C_4$—H), d 6.35 (d, J=2 Hz, 1 H, $C_6$—H), d 6.44 (b, 1 H, —S$\underline{H}$); MS m/z (relative intensity) 203 (MH$^+$, 100), 161 (48).

Anal. Calcd. for $C_9H_{11}FO_2S$: C, 53.42; H, 5.50; S, 15.86. Found: C, 53.54; H, 5.40; S, 15.64.

Example 43

3-Fluoro-2-((4-fluoro-2-nitrophenyl)thio)-5-isopropoxyphenol

Potassium tert-butoxide (0.18 g, 1.6 mmol) was added to a stirred, degassed, solution of 3-fluoro-5-isopropoxy-2-mercaptophenol (0.30 g, 1.5 mmol) (Example 42) and 2-5-difluoronitrobenzene (0.24 g, 1.5 mmol) in 10 mL anhydrous DMF at –10° C. The resulting reddish-brown reaction was stirred at –10° C. for 10 min and 1 h at room temperature then diluted with EtOAc (50 ml). The combined organics were washed with 10% aqueous HCl (50 mL) and brine (50 ml), dried ($Na_2SO_4$), and concentrated in vacuo to a yellow solid (0.53 g). Purification by radial chromatography with 40% $CH_2Cl_2$/hexane yielded 370 mg of a yellow solid as a mixture of the title compound and the disulfide of 3-fluoro-5-isopropoxy-2mercaptophenol. Crystallization from EtOAc/hexane afforded the title compound as fine, yellow needles (0.21 g, 42%): TLC ($CH_2Cl_2$/hexane 30:70) $R_f$=0.17; HPLC ($T_r$=14.4); $^1$H-NMR ($CDCl_3$) d 1.39 (d, J=6 Hz, 6 H), d 4.57 (m, 1 H), d 6.38 (dd, J=2Hz, J=11 Hz, 1 H, $C_4$—H), d 6.45 (m, 2 H), d 6.87 (m, 1 H), d 7.21 (m, 1 H); d 8.03 (dd, J=3 Hz, J=11 Hz, 1 H), $^{19}$F-NMR ($CDCl_3$) $C_3$—F (d, J=11 Hz); $C_4$—F (m); MS m/z (relative intensity) 342 (MH$^+$, 49), 300 (58), 172 (100).

Anal. Calcd for $C_{15}H_{13}F_2NO_4S$: C, 52.72; H, 3.85; N, 4.11; S, 9.40. Found: C, 52.88; H, 3.83; N, 4.16; S, 9.34.

Example 44

2,4'-Difluoro-6-hydroxy-4-isopropoxy-2'-nitrodiphenyl Sulfone

A solution of 3-fluoro-2-((4-fluoro-2-nitrophenyl)thio)-5-isopropoxyphenol (200 mg, 0.59 mmol) (Example 43) and $CH_3CO_3H$ (32% in AcOH, 0.78 ml, 3.55 mmol) in 5 mL glacial AcOH was heated at 55° C. for 5 h. The reaction was concentrated in vacuo to a deep, yellow oil and purified by radial chromatography with 40% $CH_2Cl_2$/hexane to yield 170 mg (78%) of the title compound as a yellow, waxy solid: TLC ($CH_2Cl_2$/hexane, 60:40) $R_f$=0.40; HPLC ($T_r$=13.3); $^1$H-NMR ($CDCl_3$) d 1.35 (d, J=6.1 Hz, 6 H), d 4.55 (m, 1 H), d 6.13 (dd, J=2Hz, J=12 Hz, 1 H), d 6.33 (s, 1 H), d 7.48–7.67 (m, 2 H), d 8.50 (m, 1 H); d 9.41 (s, 1 H, —O$\underline{H}$); $^{19}$F-NMR ($CDCl_3$) $C_2$—F (d, J=12 Hz); $C_{4'}$—F (m); MS m/z (relative intensity) 374 (MH$^+$, 100), 332 (21).

Anal. Calcd for $C_{15}H_{13}F_2O_6S$: C, 48.23; H, 3.52; N, 3.75; S, 8.59. Found: C, 48.17; H, 3.49; N, 3.75; S, 8.66.

Example 45

1,7-Difluoro-3-isopropoxyphenoxathiin 10,10-dioxide

A stirred solution of 2,4'-difluoro-6-hydroxy-4-isopropoxy-2'-nitrodiphenyl sulfone (150 mg, 0.46 mmol)

(Example 44) and potassium tert-butoxide (60 mg, 1.18 mmol) in 5 ml anhydrous DMF was heated at 55° C. for 90 min. After the reaction had been cooled to room temperature, it was diluted with EtOAc (50mL), washed with $H_2O$ (50 mL) and brine (50 mL), dried ($Na_2SO_4$) and concentrated in vacuo to an orange-brown oil. The crude product was purified by preparative TLC (EtOAc/hexane 15:85) and then crystallized from EtOAc/hexane to yield 35 mg (24%) of the title compound as a white solid: mp 148–151° C.; TLC (EtOAc/hexane 5:95) $R_f$=0.13; HPLC ($T_r$=13.7); $^1$H-NMR (DMSO-$d_6$) d 1.32 (d, J=6 Hz, 6 H), d 4.87 (m, 1 H), d 6.95 (d, J=2Hz, 1 H, $C_4$—H), d 7.11 (dd, J=2 Hz, J=12 Hz, 1 H, $C_2$—H), d 7.40–7.57 (m, 2 H), d 8.07 (m, 1 H, $C_9$—H); $^{19}$F-NMR (DMSO-$d_6$) $C_1$—F (d, J=12 Hz), $C_7$—F (m); MS m/z (relative intensity) 327 (MH$^+$, 100).

Anal. Calcd for $C_{15}H_{12}F_2O_4S$: C, 55.18; H, 3.72; S, 9.83. Found: C, 55.43; H, 3.67; S, 9.93.

Example 46

(rac)-3-(2,2,2-Trifluoro-1-methylethoxy) phenoxathiin 10,10-dioxide

Method A. (rac)-1,1,1-Trifluoro-2-propanol (Oakwood) (0.45 g, 0.004 mole) was added to a stirred, ice-bath cooled mixture of potassium hydride (approximate 50% dispersion in mineral oil) (Aldrich) (0.32 g, 0.004 mole) and N,N-dimethylformamide (50 mL). The ice-bath was removed, and the reaction was stirred at ambient temperature for 1 hour. 3-Fluorophenoxathiin 10,10-dioxide (Example 47) (1.00 g, 0.004 mole) was added, and the mixture was heated at reflux under nitrogen for 2 hours. The reaction was cooled, and the volatiles were removed by spin evaporation in vacuo. The residue was purified by column chromatography on Silica Gel 60 using ethyl acetate-hexanes:3–7. The appropriate column fractions were combined, and the volatiles were removed by spin evaporation in vacuo to give 1.21 g (87% yield) of (rac)-3-(2,2,2-trifluoro-1-methylethoxy) phenoxathiin 10,10-dioxide. Recrystallization from ethanol gave 1.03 g (74yield) of the analytical sample, m.p. 97–98.5° C.

Anal. Calcd for $C_{15}H_{11}F_3O_4S$: C, 52.33; H, 3.22; S, 9.31. Found: C, 52.39; H, 3.13; S, 9.22.

Method B. (rac)-1,1,1-Trifluoro-2-propanol (Oakwood) (189.30 g, 1.66 mole) in N,N-dimethylacetamide (200 mL) was added to a stirred, ice-bath cooled mixture of hexanes washed sodium hydride (60% dispersion in mineral oil) (Aldrich) (66.40 g, 1.66 mole) and N,N-dimethylacetamide (1900 mL) under nitrogen. The reaction was stirred at ambient temperature (5–20° C.) for 0.5 hour. 3-Fluorophenoxathiin 10,10-dioxide (Example 47) (277.78 g, 1.11 mole) in N,N-dimethylacetamide (1800 mL) was added at a bath temperature of 5–15° C. and stirred at ambient temperature for 1 hour. The reaction mixture was poured into water (8 L) and extracted with ethyl acetate (3 L, 2 L). The combined extracts were washed with water (4 L, 2 L), brine (0.5 L), dried over magnesium sulfate and filter. The volatiles were removed by spin evaporation in vacuo. The residue was stirred with hexanes (1 L) and collected by suction filtration to give 399.51 g of crude product. Recrystallization from 2-propanol (1.5 L) gave 304.62 g (79% yield) of (rac)-3-(2,2,2-trifluoro-1-methylethoxy)phenoxathiin 10,10-dioxide, m.p. 98–100 C.

Anal. Calcd for $C_{15}H_{11}F_3O_4S$: C, 52.33; H, 3.22; S, 9.31; F, 16.55. Found: C, 52.29; H, 3.34; S, 9.27; F, 16.82.

Example 47

S-(+)-2-(3-Phenoxathiinyloxy)propanol S,S-dioxide

2-Hydroxy thiophenol was purchased from Lancaster Synthesis Inc., Windham N.H. (S)-(+)-1,2-Propanediol and 2,5-difluoronitrobenzene were purchased from Aldrich Chemical Co., Milwaukee, Wis. Melting points are uncorrected. $^1$H NMR coupling constants are in Hz and are $^1$H—$^1$H unless noted otherwise. $^1$H NMR chemical shifts are reported in ppm relative to the solvent resonance at δ 7.26 $CDCl_3$. $^{19}$F NMR chemical shifts are reported in ppm relative to trifluoroacetic acid. Elemental analyses were performed by Atlantic Microlabs, Norcorss, Ga.

(a) 3-Fluorophenoxathiin: A solution of 2-hydroxythiophenol (22.53 g, 178.6 mmol) in DMF (125 mL potassium tert-butoxide (40.08 g, 357.1 mmol) in DMF (200 mL). The resulting mixture was stirred 10 min and a solution of 2,5-difluoronitrobenzene (28.41 g, 178.6 mmol) in DMF (125 mL) was added dropwise. The ice bath was removed and the mixture was allowed to warm to room temperature and then heated to reflux (internal temperature= 140° C.). The reaction mixture was maintained at reflux for 45 min and was then allowed to cool to room temperature. The DMF was removed by rotovac and the remaining crude material was partitioned between EtOAc and $H_2O$. The layers were separated and the EtOAc layer was washed with $H_2O$ and brine, dried over $MgSO_4$, filtered and concentrated onto silical gel (50 g). Flash chromatography on silical gel eluting with hexanes provided 3-Fluorophenoxathiin (27.5 g, 126.0 mmol, 71%) as a white solid: mp 77.5–79° C.; $^1$H NMR (CDCl$_3$) δ 7.2–6.9 (5H, m), 6.75 (2H, m);

Anal. Calcd. for $C_{12}H_7FOS$: C, 66.04; H, 3.23; S, 14.69. Found: C, 66.12; H, 3.16; S, 14.75.

(b) 3-Fluorophenoxathiin 10,10-dioxide: 30% $H_2O_2$ (70 mL) was added dropwise to a stirring, ice-cooled mixture of 3-fluorophenoxathiin (26.88 g, 123.2 mmol) and TFA (160 mL). The mixture was allowed to warm to room temperature and stirring was continued for one hour. Half of the TFA was removed by rotovac and the remaining mixture was diluted with dichloromethane and poured into a separatory funnel. The dichloromethane mixture was washed with $H_2O$. sat. $NaHCO_3$ and brine, dried over $MgSO_4$, filtered and evaporated to provide 3-fluorophenoxathiin10,10-dioxide (30.19 g, 120.6 mmol, 98%) as a white solid: mp 174.5–175.5° C., $^1$H NMR (CDCl$_3$) δ 8.07 (1H, dd, J=9, $J_{HF}$=3.9), 8.06 (1H, br d, J=8.7), 7.67 (1H, ddd, $J_{HF}$=8.7, J=7.4. 1.5), 7.42 (2H, m), 7.13 (2H, m); $^{19}$F NMR (CDCl$_3$) δ 25.79 (ddd, $J_{FH}$=9.3, 7.9, 5.9); CIMS: m/z 251 (M+1, 100);

Anal. Calcd for $C_{12}H_7FO_3S$: C, 57.60; H, 2.82; S, 12.81. Found: C, 57.44; H, 2.73; S, 12.76.

(c) (S)-(−)-1-Benzyloxy-2propanol: A mixture of powdered KOH (5.90 g, 105 mmol), (S)-(+)-1,2-propanediol (8.00 g, 105 mmol) and benzyl chloride (13.3 g, 105 mmol) was heated at 130° C. for 2 hours. The mixture was cooled to room temperature, diluted with water and extracted with $Et_2O$ layer was separated and washed with brine, dried over $MgSO_4$, filtered and concentrated to provide 14.49 g of crude product which was dissolved in dichloromethane (50 mL). Triethyl amine (4.90 g, 48.4 mmol), DMAP (0.48 g, 3.93 mmol) and tert-butyldimethylsilyl chloride (6.5 g, 43.2 mmol) were added and the resulting solution was stirred at room temperature ca. 18 hours. The solution was then washed with $H_2O$ and brine, dried over $MgSO_4$, filtered and concentrated in vacuo providing a crude oil. Flash chromatography on silica gel eluting with 27.5% EtOAc/hexanes provided (s)-(−)-1-Benzyloxy-2-propanol (4.12 g, 24.8 mmol, 24%) as a nearly colorless oil: $[\alpha]_D^{20}$=+5.36° (c=3.30, MeOH); $^1$H NMR (CDCl$_3$) δ 7.4–7.3 (5H, m), 4.56 (2H, s), 4.01 (1H, ddq, J=8.2, 6.3, 3), 3.48 (1H, dd, J=9.3, 3), 3.28 (1H, dd, J=9.3, 8.2), 2.05 (1H, br), 1.15 (3H, d, J=6.3); CIMS m/z 189 (M+23, 100);

Anal. Calcd for C$_{10}$H$_{14}$O$_2$·(0.1 H$_2$O): C, 71.49; H, 8.52; Found: C, 71.34; H, 8.51.

(d) (S)-(−)-3-((1-Benzyloxy)-2-propoxy)phenoxathiin 10,10-dioxide: A solution of (S)-(−)-1 Benzyloxy-2-propanol (4.04 g, 24.30 mmol) in DMF (30 mL) was added dropwise to an ice-cooled, stirring slurry of NaH (1.17 G, 48.61 mmol) in DMF) (30 mL). After hydrogen evolution subsided, a solution of 3-fluorophenoxathiin 10,10-dioxide (6.01 g, 24.00 mmol) in DMF (50 ml) was added dropwise. The reaction mixture was allowed to warm to room temperature and was stirred an additional 30 min. The DMF was removed by rotovac and the crude material was partitioned between EtOAc and H$_2$O. The layers were separated and the aqueous layer was extracted with EtOAc. The combined organic layers were washed with brine, dried over MgSO$_4$, filtered and concentrated in vacuo. Purification of the resulting material by flash chromatography on silica gel eluting with 35% EtOAc/hexanes provided (S)-(−)-3-((1-Benzyloxy)-2-propoxy)phenoxathiin 10,10-dioxide (8.28 g, 20.9 mmol, 87%) as a colorless, viscous oil: [α]$_D^{20}$=−18.77° (c=2.12, MeOH); $^1$H NMR (CDCl$_3$) δ 8.05 (1H, dd, J=8.1, 1.6), 7.92 (1H, d, J=9), 7.63 (1H, ddd, J=9, 7.5, 1.8), 7.42–7.26 (7H, m), 6.95 (1H, dd J=9, 2.3), 6.87 (1H, d, J=2.3), 4.69 (1H, m), 4.59 (2H, s), 3.69 (1H, dd, J=10.3, 6), 3.61 (1H, dd, J=10.3, 4.5), 1.37 (3H, d, J=6.3); CIMS m/z 419 (M+23, 46), 397 (M+1, 55), 339 (100)

Anal. Calcd. for C$_{22}$H$_{20}$O$_5$S: C, 66.65; H, 5.08; S, 8.09. Found: C, 66.45; H, 5.12; S, 8.16.

(e) (S)-(+)-2-(3-Phenoxathiinyloxy)propanol S,S-dioxide: (S)-(−)-3-((1-Benzyloxy)-2-propoxy)phenoxathiin-10,10 dioxamide (8.28 g, 20.88 mmol) was dissolved in MeOH (150 mL) with heating and 5% Pd on carbon (0.7 g) was added. The mixture was hydrogenolyzed at 45 psi for ca. 18 hours, vacuum filtered and the filtrate concentrated in vacuo. Purification of the crude material by flash chromatography on silica gel eluting with 65% EtOAc/hexanes provided (S)-(+)-2-(3-phenoxathiinyloxy)propanol S,S-dioxamide (5.21 g, 17.0 mmol, 81%) as a partially translucent, hygroscopic solid: mp 91–93° C.; [α]$_D^{20}$=+17.70° (c=4.52, MeOH); $^1$H NMR (CDCl$_3$) δ 8.06 (1H, dd, J=8, 1.5), 7.95 (1H, d, J=9), 7.64 (1H, ddd, J=8, 8, 1.5), 7.40 (1H, ddd, J=8, 8, 1), 7.36 (1H, dd, J=8, 1), 6.98 (1H, dd, J=9, 2.3), 6.87 (1H, d, J=2.3), 4.62 (1H, hex, J=6), 3.80 (2H, t, J=6), 1.92 (1H, t, J=6), 1.35 (3H, d, J=6); CIMS m/z 329 (M+23, 29), 307 (M+1, 19), 249 (100)

Anal. Calcd. for C$_{15}$H$_{14}$O$_5$S·(0.1 H$_2$O): C, 58.47; H, 4.64; S, 10.41. Found: C, 58.30; H, 4.67; S, 10.30.

Example 48

2-Bromo-3-isopropoxynitrobenzene

BBr$_3$ (1 M in CH$_2$Cl$_2$, 77 mL, 77 mmol) was added dropwise, over 1 h, to a stirred solution of 4-bromo-3-nitroanisole (5.0 g, 22 mmol) in 30 mL CH$_2$Cl$_2$ at −70° C. under nitrogen. The resulting deep burgundy-colored reaction was stirred overnight (23 h) and then poured onto 300 g crushed ice. EtOAc (250 mL) was added and the organic fraction washed with brine (250 mL), dried (MgSO$_4$) and concentrated in vacuo to 5.06 g of a yellow-brown solid. Purification by column chromatography (EtOAc/hexane, gradient elution 5:95 to 15:85) afforded 3.77 g (79%) of 2-bromo-3-nitrophenol as a yellow solid: TLC (EtOAc/hesane 20:80) R$_f$=0.12; HPLC (T$_r$=12.2); $^1$H-NMR (CDCl$_3$) δ 5.57 (s, 1H, —OH), δ 6.95 (dd, J=8 Hz, J=3 Hz, 1H), δ 7.36 (d, J=3 Hz, 1H), δ 7.58 (d, J=8 Hz, 1H); MS m/z (relative intensity) 218 (MH$^+$, 100), 220 (MH$^+$+2.56).

Anal. Calcd. for C$_6$H$_4$BrNO$_3$: C, 33.06; H, 1.85; N, 6.42; Br, 36.65 Found: C, 33.14; H, 1.86; N, 6.38; Br, 36.57.

Cs$_2$CO$_3$ was added in 3 portions over 15 min to a stirred solution of 2-bromo-3 nitrophenol (3.00 g, 13.8 mmol) and 2-iodopropane (4.79 g, 27.6 mmol) in 50 ml anhydrous DMF cooled to 0° C. under N$_2$. The reaction was allowed to warm to ambient temperature (2 h) and stirred overnight (17 h). EtOAc (250 ml) was added, the reaction mixture washed with water (2×250 ml) and brine (250 ml), dried (Na$_2$SO$_4$) and concentrated in vacuo to an orange oil (3.78 g). Purification by column chromatography (EtOAc/hexane, 5:95) afforded 3.49 g (97%) of 2-bromo-3-isopropoxynitrobenzene as a yellow oil. TLC (EtOAc/hexane 20:80)R$_f$=0.12; HPLC (T$_r$=16.1); $^1$H-NMR (CDCl$_3$) d 1.35 (d, J=6 Hz, 6H), δ 4.56 (m, J=6 Hz, 1H), δ 6.95 (dd, J=8 Hz, J=3 Hz, 1H), δ 7.34 (d, J=3 Hz, 1H), δ 7.57 (d, J=8 Hz, 1H): MS m/z (relative intensity) 260 (MH$^+$, 100), 262 (MH$^+$+2, 72).

Anal. Calcd. for C$_9$H$_{10}$BrNO$_3$: C, 41.56; H, 3.88; N, 5.39; Br, 30.72. Found: C, 42.47; H, 3.98; N, 5.24; Br, 30.04.

Example 49

3-Methoxy-(4-trimethylsilyl)phenoxathiin

A solution of sec-butyllithium (4.00 ml of a 1.3 M solution in cyclohexane, 5.2 mmol) was added dropwise, over 15 min, to a stirred solution of 3-methoxyphenoxathiin (1.00 g, 4.3 mmol) and TMEDA (0.79 ml, 5.2 mmol) in 15 ml anhydrous THF at −65° C. (internal bath temperature). The pale, yellow solution was stirred at −60 to −70° C. for 45 min followed by addition of TMSCl (0.82 ml, 6.51 mmol). After stirring at −60° C. for 45 min the reaction was allowed to warm to ambient temperature over 1 h. Saturated aqueous NH$_4$Cl (30 ml) was added followed by EtOAc (50 ml) and H$_2$O (25 ml). The organic layer was washed with saturated brine solution (50 ml), dried over Na$_2$SO$_4$, and concentrated in vacuo to a colorless oil (1.24 g). Purification by column chromatography (hexane) afforded 1.17 g (89%) of 3-methoxy-(4-trimethylsilyl)phenoxathiin as a colorless oil: TLC (hexane) R$_f$=0.22; $^1$H-NMR (CDCl$_3$) δ 0.40 (s, 9H), δ 3.74 (s, 3H), δ 6.54 (d, J=8.5 Hz, 1H, C$_2$—H, δ 7.00–7.12 (m, 5H); MS m/z (relative intensity) 302 (M$^+$, 100), 287 (91).

Anal. Calcd for C$_{16}$H$_{18}$O$_2$Ssi: C, 63.51; H, 6.01; S, 10.60. Found: C, 63.37; H, 6.09; S, 10.55.

Example 50

1-Fluoro-3-methoxy-4-(trimethylsilyl)phenoxathiin

A solution of sec-butyllithium (4.02 ml of a 1.3 M solution in cyclohexane 2.6 mmol) was added dropwise, over 15 min, to a stirred solution of 3-methoxy-(4-trimethylsilyl)phenoxathiin (0.66 g, 2.2 mmol) and TMEDA (0.40 ml, 2.62 mmol) in 10 ml anhydrous THF at −65° C. (internal bath temperature). The pale, yellow solution was stirred at −60 to −70°C. for 1 h followed by dropwise addition of N-fluorobenzenesulfonimide (1.03 g, 3.27 mmol) in 5 ml anhydrous THF. The reaction was allowed to warm to −45° C. over 1 h. Saturated aqueous NH$_4$Cl (30 ml) was added and the resulting heterogeneous mixture stirred at ambient temperature overnight (16 h). EtOAc (50 ml) and H$_2$O (25 ml) were added, the organic layer washed with brine (50 ml), dried (Na$_2$SO$_4$), and evaporated to dryness in vacuo to a tan solid (1.10 g). The solid was triturated with hexane (2×50 ml) and the combined hexane washings concentrated in vacuo to a yellow oil (0.69 g). Purification by column chromatography (hexane) afforded 243 mg (35%) of 1-fluoro-3-methoxy-4-(trimethylsilyl)phenoxthiin as a colorless oil followed by 175 mg (30%) of unreacted 3-methoxy-(4-trimethylsilyl)phenoxathiin:TLC (hexane) $R_f$=0.19; $^1$H-NMR (CDCl$_3$) δ 0.39 (s, 9H), δ 3.73 (s, 3H), δ 6.38 (d, J=11 Hz, 1H, C$_2$—H), δ 7.01–7.16 (m, 4H); MS m/z (relative intensity) 321 (MH$^+$, 100), 305 (95).

Example 51

1-Fluoro-3-methoxyphenoxathiin

A solution of 1-fluoro-3-methoxy-4-(trimethylsilyl) phenoxathiin (120 mg, 0.37 mmol) and CsF (110 mg, 0.74 mmol) in 3 ml 10% (v/v) aqueous DMF was heated under nitrogen at 100° C. for 1 h. After cooling to room temperature, the reaction was diluted with Et$_2$O (30 ml) and H$_2$O (30 ml). The Et$_2$O layer was washed with brine (30 ml), dried (Na$_2$SO$_4$), and concentrated in vacuo to a yellow oil (92 mg). Filtration of the crude product through silica gel (10 g) with 100 ml of 4:1 hexane:CH$_2$Cl$_2$ yielded 88 mg (96%) of 1-fluoro-3-methoxy-4-(trimethylsily)phenoxathiin as a colorless oil. TLC (CH$_2$Cl$_2$/hexane, 10:90) $R_f$=0.27; $^1$H-NMR (CDCl$_3$) δ 3.77 (s, 3H), δ 6.38 (dd, J=12 Hz, J=2.5 Hz, 1H, C$_2$—H), δ 6.43 (d, J=2.5 Hz, 1H, C$_4$—H), δ 6.95–7.12 (m, 4H); $^{19}$F-NMR (CDCl$_3$) C$_1$—F (dd, J=12 Hz, J=2.5 Hz); MS m/z (relative intensity) 249 (MH$^+$, 100).

Example 52

1-Fluoro-3-methoxyphenoxathiin 10,10-dioxide

A solution of 1-fluoro-3-methoxyphenoxathiin 10,10-dioxide (86 mg, 0.35 mmol) and 30% aqueous H$_2$O$_2$ (0.40 g, 3.5 mmol) in 3 ml glacial AcOH was heated at 90° C. for 90 min. After cooling to room temperature a white solid crystallized and water (50 ml) was added to complete precipitation. The crude product was filtered and dried overnight in vacuo (0.1 mm). Purification by column chromatography (70:30 CH$_2$Cl$_2$/hexane) yielded 60 mg (60%) of 1-fluoro-3-methoxyphenoxathiin 10,10 dioxide as white powder: mp 226–230° C.; TLC (CH$_2$Cl$_2$/hexane, 50:50) $R_f$=0.12; $^1$H-NMR (DMSO-d6) δ 3.93 (s, 3H), δ 7.00 (d, J=2 Hz, 1H, C$_4$—H), δ 7.11 (dd, J=2.5 Hz, J=12 Hz, 1H, C$_2$—H), δ 7.53–7.59 (m, 2H), δ 7.84 (dt, J=8 Hz, J=2 Hz, 1H, C$_8$—H), δ 8.07 (dt, J=8 Hz, J=2 Hz, 1H, C$_9$—H); $^{19}$F-NMR (DMSO-d$_6$) C$_1$—F (d, J=13 Hz); MS m/z (relative intensity) 281 (MH$^+$, 100).

Anal. Calcd for C$_{13}$H$_9$FO$_4$S: C, 55.71; H, 3.24; S, 11.44. Found: C, 55.47; H, 3.21; S, 11.33.

Example 53

3-Methoxyphenoxathiin

A stirred, degassed, solution of 2-hydroxythiophenol (9.50, 75.3 mmol) and 3-nitro-1-bromoanisole (17.46 g, 75.29 mmol) in 150 mL DMF was cooled to −20° C. under N$_2$ and Potassium tert-butoxide added, as solid, in 10 portions over 15 min. The brown-black reaction mixture was allowed to warm to 20° C. over 20 min and then placed in an oil bath at 150° C. overnight (20 h). The solvent was vacuum distilled at 40° C. (1.0 mm) and the brown residue (57 g) chromatographed on 500 g silica gel with CH$_2$Cl$_2$/hexane (5:95) to afforded 13.5 g of a colorless oil. Short path distillation (160° C., 0.15 mm) yielded 12.49 g (72%) of 3-methoxyphenoxathiin as a waxy solid: TLC (EtOAc/hexane (2:98) $R_f$=0.21; HPLC (T$_r$=17.3), $^1$H-NMR (CDCl$_3$) δ 3.79 (s, 3H), δ 6.59–6.63 (m, 2H, C$_2$— and C$_4$—H), δ 6.97–7.12 (m, 5H); MS m/z (relative intensity) 231 (MH$^+$, 100).

Anal. Calcd for C$_{13}$H$_{10}$O$_2$S: C, 67.80; H, 4.39; S, 13.92. Found: C, 67.83; H, 4.40; S, 13.86.

Example 54

3-Phenoxathiinol

A stirred 3-methoxyphenoxathiin (3.00, 13.03 mmol) 25 ml CH$_2$Cl$_2$ was cooled to −70° C. under N$_2$ and BBr$_3$ (45.6 ml, 45.6 mmol, 1.0 M in CH$_2$Cl$_2$) was added dropwise over 1 h. The resulting bright, blue, heterogeneous mixture was allowed to warm to room temperature and stirred overnight. After 21 h the yellow homogeneous reaction is cooled to −60° C. and poured onto 300 mL MeOH at −60° C. After warming to room temperature the solution was concentrated in vacuo to a dark yellow oil which was purified by column chromatography (CH$_2$Cl$_2$/hexane, gradient elution, 50:50 to 100:00) to give 2.59 g (91%) 3-phenoxathiinol as a white solid. TLC (CH$_2$Cl$_2$/hexane 50:50) $R_f$=0.14; HPLC (T$_r$=14.2), $^1$H-NMR (CDCl$_3$) δ 4.78 (s, 1H, —OH), δ 6.52 (d, J=8 Hz, 1H, C$_2$—H), δ 6.56 (s, 1H, C$_4$—H), δ 6.92–7.14 (m, 5H); MS m/z (relative intensity) 217 (MH$^+$, 100).

Anal. Calcd for C$_{12}$H$_8$O$_2$S: C, 66.64; H, 3.74; S, 14.82. Found: C, 66.55; H, 3.78; S, 14.92.

Example 55

3-(2,2,2-Trifluoroethoxy)phenoxathiin 10,10-dioxide

Method A. 1,1,1-Trifluoro-2-ethanol (Aldrich) (0.44 g, 0.004 mole) was added to a stirred, ice-bath cooled mixture of potassium hydride (approximate 50% dispersion in mineral oil) (Aldrich) (0.32 g, 0.004 mole) and N,N-dimethylformamide (75 mL). The ice-bath was removed, and the reaction was stirred at ambient temperature for 1 hour. 3-Fluorophenoxathiin 10,10-dioxide (Example 47) (1.00 g, 0.004 mole) was added, and the mixture was heated at reflux under nitrogen for 2 hours. The reaction was cooled, and the volatiles were removed by spin evaporation in vacuo. The residue was purified by column chromatography on Silica Gel 60 using ethyl acetate-hexanes:2–8. The appropriate column fractions were combined, and the volatiles were removed by spin evaporation in vacuo to give 0.43 g (32% yield) of 3-(2,2,2-trifluoroethoxy)phenoxathiin 10,10-dioxide. Recrystallization from ethanol gave 0.23 g (17% yield) of 3-(2,2,2-trifluoroethoxy)phenoxathiin 10,10-dioxide, m.p. 165–166° C.

Anal. Calcd for C$_{15}$H$_9$F$_3$O$_4$S: C, 50.91; H, 2.75; S, 9.71. Found: C, 50.99; H, 2.80; S, 9.83.

Method B. 3-Fluorophenoxathiin 10,10-dioxide (Example 47) (6.27 g, 0.025 mmol) was added to a stirred solution prepared from 1,1,1-trifluoro-2-ethanol (Aldrich) (2.64 g, 0.0264 mole), potassium tert-butoxide (Janssen) (2.96 g, 0.0264 mole) and dry acetonitrile (170 mL). The mixture was heated at reflux under nitrogen for 1 hour. The reaction was cooled, and the volatiles were removed by spin evaporation in vacuo. The residue was partitioned between dichloromethane (200 mL) and water (100 mL). The layers were separated, and the organic phase was washed with 0.1 N aqueous hydrogen chloride (75 mL), brine (75 mL) and then dried over magnesium sulfate. The dry solution was spin evaporated in vacuo to give a fluffy residue, which was recrystallized from ethanol to give 6.40 g (77% yield) of 3-(2,2,2-trifluoroethoxy)phenoxathiin 10,10-dioxide, m.p. 167–168° C.

Anal. Calcd for C$_{15}$H$_9$F$_3$O$_4$S: C, 50.91; H, 2.75; S, 9.71. Found: C, 50.98; H, 2.73; S, 9.67.

Example 56

3-(2-Fluoro-1-(fluoromethyl)ethoxy)phenoxathiin 10,10-dioxide was made analogously to Example 55 but using 1,3-difluoro-2-propanol (Fluorochem Limited) rather than 1,1,1-trifluoro-2-ethanol and initially cooling the reaction in an ice bath for 1 hour before refluxing for 2 hours. Chromatography (silica gel, dichloromethane) gave a solid with m.p. 156–158° C.

Anal. Calcd for $C_{15}H_{12}F_2O_4S$: C, 55.21; H, 3.71; S, 9.82. Found: C, 55.24; H, 3.68; S, 9.70.

Example 57

3-(2,2-(Difluoro)-1-(difluoromethyl)ethoxy)phenoxathiin 10,10-dioxide was made analogously to Example 55 but using 1,1,3,3-tetrafluoro-2-propanol rather than 1,1,1-trifluoroethanol. Chromatography (silica gel, ethyl acetate:hexanes/20:80) gave a solid with m.p. 90–92° C.

Anal. Calcd for $C_{15}H_{10}F_4O_4S$: C, 49.73; H, 2.78; S, 8.85. Found: C, 49.90; H, 2.90; S, 8.97.

Example 58

(rac)-3-(1-(Difluoromethyl)ethoxy)phenoxathiin 10,10-dioxide was made analogously to Example 55 but using (rac)-1,1-difluoro-2-propanol rather than 1,1,1-trifluoroethanol. Chromatography (silica gel, dichloromethane) and recrystallization from 2-propanol gave a solid with m.p. 111–113° C.

Anal. Calcd for $C_{15}H_{12}F_2O_4S$: C, 55.21; H, 3.71; S, 9.82. Found: C, 55.11; H, 3.72; S, 9.86.

Example 59

(rac)-2-(3-Phenoxathiinyloxy)-2-(trifluoromethyl) ethanol S,S-dioxide a) Preparation of (rac)-3,3,3-trifluoro-1,2-propanediol A slurry of potassium osmate(VI) dihydrate (Aldrich) (0.30 g, 0.81 mmol), potassium carbonate (12.9, 93.47 mmol) and potassium ferricyanide (Acros) (30.8 g, 93.53 mmol) in water (90 mL) was added slowly to a saturated solution of 3,3,3-trifluoropropene (Aldrich) (4.0 g, 41.6 mmol) in t-butyl alcohol (120 mL). The reaction mixture was stirred at ambient temperature in a thick-walled, Teflon screw-capped vessel for 48 h. The reaction mixture was vacuum filtered through a pad of Celite which was washed with brine (500 mL) and then ethyl acetate (750 mL). The combined filtrates were separated, and the aqueous layer was extracted with ethyl acetate (250 mL). The combined organic solutions were washed with brine, dried over magnesium sulfate and spin evaporated to give a light-brown oil. The oil was dried in vacuo to give 4.07 g (75%) of (rac)-3,3,3-trifluoro-1,2-propanediol.

b) Preparation of (rac)-3,3,3-trifluoro-1-triphenylmethoxy-2-propanol

A solution of (rac)-3,3,3-trifluoro-1,2-propanediol (4.07 g, 31.3 mmol) and triphenylmethyl chloride (Aldrich) (8.72 g, 31.3 mmol) in pyridine (25 mL) was stirred at ambient temperature for 16 h. The volatiles were removed by spin evaporation, and the residue was dissolved in ether (250 mL). This solution was washed twice with 1N hydrochloric acid, once with brine, dried over magnesium sulfate, and spin evaporated to give an orange oil which was a 2:1 mixture of 3,3,3-trifluoro-1,2-propanediol and 3,3,3-trifluoro-1-triphenylmethoxy-2-propanol. The mixture was redissolved in pyridine (25 mL) and triphenylmethyl chloride (4.51 g, 16.1 mmol) was added. The solution was stirred at ambient temperature for 16 h. The volatiles were removed by spin evaporation, and the residue was partitioned between ethyl acetate and brine. The layers were separated, and the brine fraction was extracted with ethyl acetate. The organic layers were combined, dried over magnesium sulfate and spin evaporated to give an oil. This crude product was purified by flash column chromatography (15% ethyl acetate:hexanes) to give 6.3 g (54%) of (rac)-3,3,3-trifluoro-1-triphenylmethoxy-2-propanol as a thick, colorless oil.

c) Preparation of (rac)-2-(3-phenoxathiinyloxy)-2-(trifluoromethyl)-1-triphenylmethoxyethane S,S-dioxide A solution of (rac)-3,3,3-trifluoro-1-triphenylmethoxy-2-propanol (6.33 g, 17.0 mmol) in N,N-dimethylformamide (25 mL) was added drop wise to a stirred slurry of sodium hydride (0.82 g, 34 mmol) in N,N-dimethylformamide (15 mL) cooled in an ice-bath. After 5 minutes, a solution of 3-fluorophenoxathiin 10,10-dioxide in N,N-dimethylformamide (20 mL) was added drop wise, and the reaction mixture was stirred at ambient temperature for a few hours. The reaction was diluted with water (200 mL) and extracted with ether (4×250 mL). The combined extracts were washed with water, brine, dried over magnesium sulfate and spin evaporated to give 3.9 g (40%) of (rac)-2-(3-phenoxathiinyloxy)-2-(trifluoromethyl-1-triphenylmethoxyethane S,S-dioxide as a crude oil.

d) Preparation of (rac)-2-(3-phenoxathiinyloxy)-2-(trifluoromethyl)ethanol S,S-dioxide A solution of (rac)-2-(3-phenoxathiinyloxy)-2-(trifluoromethyl)ethanol S,S-dioxide (3.9 g, 6.47 mmol) and p-toluenesulfonic acid (1.85 g, 9.71 mmol) in methanol (24 mL):dichloromethane (8 mL) was stirred at ambient temperature for 16 h. Additional p-toluenesulfonic acid (0.62 g, 3.24 mmol) was added, and the reaction was stirred at ambient temperature for 16 h. The reaction was diluted with dichloromethane (200 mL) and absorbed on silica gel. The material was purified by flash column chromatography on silica gel (40% ethyl acetate:hexanes) to give 0.909 g (39%) of (rac)-2-(3-phenoxathiinyloxy)-2-(trifluoromethyl)ethanol S,S-dioxide, m.p. 131–132.5° C. Material from another preparation had m.p. 133–135° C.

Anal. Calcd for $C_{15}H_{11}F_3O_5S$: C, 50.00; H, 3.08; S, 8.90. Found: C, 49.95; H, 3.04; S, 8.96.

Example 60

(rac)-3-(2-fluoro-1-(trifluoromethyl)ethoxy) phenoxathiin 10,10-dioxide

A solution of (rac)-2-(3-phenoxathiinyloxy)-2-(trifluoromethyl)ethanol S,S-dioxide (0.186 g, 0.516 mmol) in dichloromethane (3.5 mL) was added dropwise to a solution of diethylaminosulfur trifluoride (DAST) (Aldrich) (0.08 mL) in dichloromethane (2 mL) that was cooled to −78+C. The reaction was brought to ambient temperature and stirred for 23 h. The reaction was quenched with water (0.5 mL) with vigorous stirring. The reaction was diluted with dichloromethane (25 mL) and water (5 mL). The layers were separated, and the aqueous portion extracted with dichloromethane (10 mL). The combined dichloromethane portions were dried (magnesium sulfate) and spin evaporated to give an oil. The oil was purified by flash column chromatography on silica gel with a 10% to 23% ethyl acetate:hexanes gradient. The fractions that contained product were combined and spin evaporated to give 0.094 g (50%) of (rac)-3-(2-fluoro-1-(trifluoromethyl)ethoxy) phenoxathiin 10,10-dioxide as an oil that crystallized under dichloromethane:hexanes; m.p. 97–100° C. Additional chromatography gave an analytical sample, m.p. 102–103° C.

Anal. Calcd for $C_{15}H_{10}F_4O_4S$: C, 49.73; H, 2.78; S, 8.85. Found: C, 49.83; H, 2.73; S, 8.76.

Example 61

(rac)-3-(1-(Fluoromethyl)ethoxy)phenoxathiin 10,10-dioxide was made analogously to Example 51 but using (rac)-2-(3-phenoxathiinyloxy)propanol S,S-dioxide (Example 37) rather than (rac)-2-(3-phenoxathiinyloxy)-2-(trifluoromethyl)ethanol S,S-dioxide. Chromatography (silica gel, methylene chloride) and recrystallization from ethyl acetate:hexanes gave a solid with m.p. 121–122.5° C.

Anal. Calcd for $C_{15}H_{13}FO_4S$: C, 58.43; H, 4.25; S, 10.40. Found: C, 55.30; H, 4.14; S, 10.50.

Example 62

(R*)-3-(2,2,2-Trifluoro-1-methylethoxy)phenoxathiin 10,10-dioxide and (S*)-3-(2,2,2-trifluoro-1-methylethoxy)phenoxathiin 10,10-dioxide Three solutions of (rac)-3-(2,2,2-trifluoro-1-methylethoxy)phenoxathiin 10,10-dioxide (Example 46) (40 mg, 40 mg, 42 mg; 0.35 mmoles total) in 2-propanol-hexanes:1-1 (1.2 mL each) were injected on a Daicel Chiralpak AS (amylose carbamate) column (2.0 cm×25.0 cm/10 micron) attached to a Waters Prep LC 2000/490 UV Detector with prep cell/746 Data Module with a fraction collector. The system was eluted with 2-propanol-hexanes:1-1 with a flow rate of 8.0 mL/min to give two well resolved peaks with elution times of 11.7 minutes (peak A) and 17.1 minutes (peak B). The appropriate fractions were combined, and the volatiles were evaporated to give peak A (35 mg) and peak B (41 mg) as clear oils. An additional chromatography was performed on (rac)-3-(2,2,2-trifluoro-1-methylethoxy)phenoxathiin 10,10-dioxide (39 mg, 38 mg; 0.22 mmoles total) under identical conditions. The two product peaks were combined with the first peak A and peak B material. The combined oils were tritutated with dichloromethane-hexanes to give white solids, which were dried in vacuo to give 58.1 mg (29% yield) of (R*)-3-(2,2,2-trifluoro-1-methylethoxy)phenoxathiin 10,10-dioxide, and 63.8 mg (32% yield) of (S*)-3-(2,2,2-trifluoro-1-methylethoxy)phenoxathiin 10,10-dioxide.

Anal. Calcd for $C_{15}H_{11}F_3O_4S$: C, 52.33; H, 3.22. Found: C, 52.38; H, 3.31 for (R*)-3-(2,2,2-trifluoro-1-methylethoxy)phenoxathiin 10,10-dioxide and Found: C, 52.32; H, 3.28 for (S*)-3-(2,2,2-trifluoro-1-methylethoxy)phenoxathiin 10,10-dioxide.

Example 63

3-Fluoro-7-hydroxyphenoxathiin 10,10-dioxide

A mixture of 3-fluoro-7-isopropoxyphenoxathiin 10,10-dioxide (Example 9) (3.51 g, 11.39 mmoles), tetrabutylammonium hydrogen sulfate (Aldrich) (0.654 g, 1.93 mmoles) and 48% aqueous hydrogen bromide (Acros) (80 mL) was refluxed with stirring for 45 minutes. The reaction was allowed to cool on an ice-bath, and the solid was collected, washed with water and dried in vacuo to give 3.010 g (99%) of 3-fluoro-7-hydroxyphenoxathiin 10,10-dioxide, mp 258–260° C. Recrystallization from ethyl acetate:hexanes gave the analytical sample, m.p. 250–260° C.

Anal. Calcd for $C_{12}H_7FO_4S$: C, 54.13; H, 2.65; S, 12.04. Found: C, 54.09; H, 2.57; S, 12.14.

Example 64

3-Fluoro-7-(2,2,2-trifluoroethoxy)phenoxathiin 10,10-dioxide

Solid 3-fluoro-7-hydroxyphenoxathiin 10,10-dioxide (Example 64) (1.092 g, 4.10 mmoles) was added to an ice-bath cooled, stirred mixture of sodium hydride (60% dispersion in mineral oil) (Aldrich) (0.164 g, 4.10 mmole) in N,N-dimethylformamide (20 mL). After 10 minutes, within which effervescence ceased, 2-iodo-1,1,1-trifluoroethaane (4.993 g, 23.78 mmoles) was added and the solution was heated with stirring at 100° C. for 24 hours. The reaction was cooled and added in portions to 100 mL of vigorously stirred ice-water to give a solid, which was collected by suction filtration and washed with water. The solid which was two equal size spots on tlc (silica gel, ethyl acetate-hexanes:1-4) dissolved in dichloromethane (50 mL), absorbed on silica gel 60 and purified by flash column chromatography on silica gel 60. The column was eluted with ethyl acetate-hexanes:1-6 (1 L) and ethyl acetate-hexanes:1-3 (1 L), and the fractions that contained product (the higher Rf spot on tlc) were combined and spin evaporated in vacuo to give 0.731 g (51% yield) of 3-fluoro-7-(2,2,2-trifluoroethoxy)phenoxathiin 10,10-dioxide as a white powder, m.p. 160–161° C.

Anal. Calcd for $C_{15}H_8F_4O_4S$: C, 48.28; H, 2.32; S, 9.21. Found: C, 48.36; H, 2.33; S, 9.22.

That which is claimed is:

1. A compound of formula (I) and prodrugs thereof:

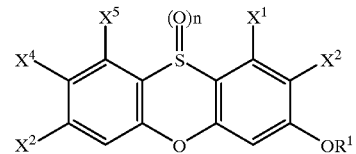

wherein n is 0, 1 or 2;

$R^1$ is a branched or straight chain C1–5 alkyl or C3–6 cycloalkyl optionally substituted with hydroxyl, or one or more halogens; and $X^1$, $X^2$, $X^3$, $X^4$, and $X^5$ are either all hydrogens or one or two of $X^1$, $X^2$, $X^3$, $X^4$ and $X^5$ are halogen and the remainder are hydrogens, with the proviso that when n is 0 or 1 and each X is hydrogen, $R^1$ is not methyl.

2. A compound according to claim 1, wherein n is 2.

3. A compound according to claim 1, wherein $R^1$ is branched or straight chain $C_{1-2}$ alkyl.

4. A compound according to claim 3, wherein $R^1$ is isopropyl.

5. A compound according to claim 1, wherein one or two of $X^1$, $X^2$, $X^3$, $X^4$ and $X^5$ are halogen.

6. A compound according to claim 1, wherein the halogen is fluorine.

7. A compound of formula (I) according to claim 1 selected from:

3-(2,2,2-trifluoroethoxy)phenoxathiin 10,10-dioxide;

3-(2,2-difluoro)-1-(difluoromethyl)ethoxy)phenoxathiin 10,10-dioxide;

(rac)-3-(1-(difluoromethyl)ethoxy)phenoxathiin 10,10-dioxide;

(rac)-3-(2-fluoro-1-(trifluoromethyl)ethoxy)phenoxathiin 10,10-dioxide;

(rac)-3-(1-(fluoromethyl)ethoxy)phenoxathiin 10,10-dioxide;

(rac)-2-(3-phenoxathiinyloxy)-2-(trifluoromethyl)ethanol S,S-dioxide;

3-(1-(fluoromethyl)ethenyloxy)phenoxathiin 10,10-dioxide;

3-isopropoxyphenoxathiin 10,10-dioxide;

7-fluoro-3-isopropoxyphenoxathiin 10,10-dioxide;
(rac)-2-(3-phenoxathiinyloxy)propanol S,S-dioxide;
1,7-difluoro-3-isopropoxyphenoxathiin 10,10-dioxide;
1-fluoro-3-isopropoxyphenoxathiin 10,10-dioxide;
2,7-difluoro-3-isopropoxyphenoxathiin 10,10-dioxide;
9-fluoro-3-isopropoxyphenoxathiin 10,10-dioxide;
(rac)-3-(2,2,2-trifluoro-1-methylethoxy)phenoxathiin 10,10-dioxide;
3-[2-fluoro-1-(fluoromethyl)ethoxy]phenoxathiin, 10,10-dioxide;
(R*)-3-(2,2,2-trifluoro-1-methylethoxy)phenoxathiin 10,10-dioxide;
(S*)-3-(2,2,2-trifluoro-1-methylethoxy)phenoxathiin 10,10-dioxide; and
3-fluoro-7-(2,2,2-trifluoroethoxy)phenoxathiin 10,10-dioxide.

8. The compound (rac)-3-(2,2,2-trifluoro-1-methylethoxy)phenoxathiin 10,10-dioxide.

9. The compound 3-(2,2,2-trifluoroethoxy)phenoxathiin 10,10-dioxide.

10. A pharmaceutical formulation comprising a compound according to claim 1 and a pharmaceutically acceptable carrier therefore.

11. A pharmaceutical formulation according to claim 10 which is a tablet or capsule.

12. A method for treating a mammal having depression which comprises administering to said mammal an effective anti-depression treatment amount of a compound of formula (I)

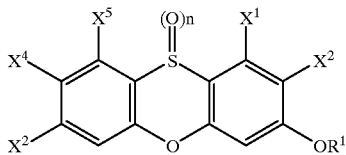

wherein n is 0, 1 or 2;
$R^1$ is a branched or straight chain C1–5 alkyl or C3–6 cycloalkyl optionally substituted with hydroxyl, or one or more halogens; and
$X^1$, $X^2$, $X^3$, $X^4$, and $X^5$ are either all hydrogens or one or two of $X^1$, $X^2$, $X^3$, $X^4$ and $X^5$ are halogen and the remainder are hydrogen, or a prodrug thereof.

13. A method for treating a mammal having depression which comprises administering to said mammal an effective anti-depression treatment amount of a compound according to claim 8.

14. A method for treating a mammal having depression which comprises administering to said mammal an effective anti-depression treatment amount of a compound according to claim 9.

15. A method for treating a mammal having anxiety which comprises administering to said mammal an effective anti-anxiety treatment amount of a compound of formula (I)

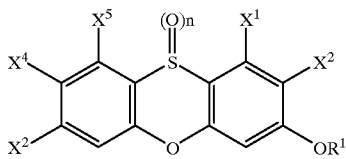

wherein n is 0, 1 or 2;
$R^1$ is a branched or straight chain C1–5 alkyl or C3–6 cycloalkyl optionally substituted with hydroxyl, or one or more halogens; and
$X^1$, $X^2$, $X^3$, $X^4$, and $X^5$ are either all hydrogens or one or two of $X^1$, $X^2$, $X^3$, $X^4$ and $X^5$ are halogen and the remainder are hydrogen, or a prodrug thereof.

16. A method for treating a mammal having a condition responsive to inhibition of MAO-A which comprises administering to said mammal an effective MAO-A inhibiting amount of a compound of formula (I)

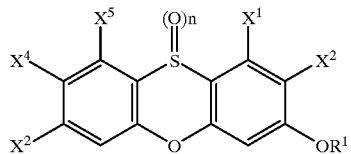

wherein n is 0, 1 or 2;
$R^1$ is a branched or straight chain C1–5 alkyl or C3–6 cycloalkyl optionally substituted with hydroxyl, or one or more halogens; and
$X^1$, $X^2$, $X^3$, $X^4$, and $X^5$ are either all hydrogens or one or two of $X^1$, $X^2$, $X^3$, $X^4$ and $X^5$ are halogen and the remainder are hydrogen, or a prodrug thereof.

17. A method of preparing a compound of formula (I)

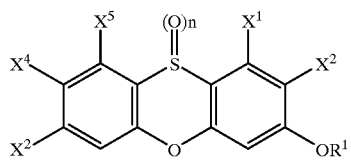

wherein n is 0, 1 or 2;
$R^1$ is a branched or straight chain C1–5 alkyl or C3–6 cycloalkyl optionally substituted with hydroxyl, or one or more halogens; and
$X^1$, $X^2$, $X^3$, $X^4$, and $X^5$ are either all hydrogens or one or two of $X^1$, $X^2$, $X^3$, $X^4$ and $X^5$ are halogen and the remainder are hydrogen, or a prodrug thereof, said method comprising the steps of:
(i) Oxidizing a diaryl sulfide to the corresponding sulfone; and
(ii) Cyclizing the sulfone to the phenoxathiin S,S-dioxide with base.

18. The compound 3-fluoro-7-(2,2,2-trifluoroethoxy)phenoxathiin 10,10-dioxide.

19. The method of claim 12 wherein the compound is 3-fluoro-7-(2,2,2-trifluoroethoxy)phenoxathiin 10,10-dioxide.

20. The method of claim 15 wherein the compound is 3-fluoro-7-(2,2,2-trifluoroethoxy)phenoxathiin 10,10-dioxide.

21. The method of claim 15 wherein the compound is 3-(2,2,2-trifluoroethoxy)phenoxathiin 10,10-dioxide.

22. The method of claim 16 wherein the compound is 3-fluoro-7-(2,2,2-trifluoroethoxy)phenoxathiin 10,10-dioxide.

23. The method of claim 16 wherein the compound is 3-(2,2,2-trifluoroethoxy)phenoxathiin 10,10-dioxide.

* * * * *

UNITED STATES PATENT AND TRADEMARK OFFICE
CERTIFICATE OF CORRECTION

PATENT NO. : 6,110,961

DATED : August 29, 2000

Page 1 of 2

INVENTOR(S) : Helen Lyng White (deceased); Morton Harfenist; Eric Boros; Dennis Heyer It is certified that error appears in the above-identified patent and that said Letters Patent is hereby corrected as shown below:

Title page, [54] in the Title "PHENOXATHIN" should read --PHENOXATHIIN--.

Title page, [56] References Cited, FOREIGN PATENT DOCUMENTS, "0 150 891 of 0000" should read --0 150 891 8/1985--; "0 419 157 of 0000" should read --0 419 157 3/1991--; "WO92 04897 of 0000" should read --WO92 04897 4/1992--; "99/13879 3/1999" should read --WO99/13879 3/1999--.

Column 1, line 1, "PHENOXATHIN" should read --PHENOXATHIIN--.

Column 2, lines 6-12, and in Claims 1, 12, 15, 16 and 17, formula (I) should appear as follows:

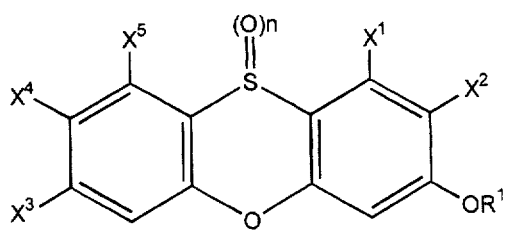

UNITED STATES PATENT AND TRADEMARK OFFICE
CERTIFICATE OF CORRECTION

PATENT NO. : 6,110,961
DATED : August 29, 2000
INVENTOR(S) : Helen Lyng White (deceased); Morton Harfenist; Eric Boros; Dennis Heyer It is certified that error appears in the above-identified patent and that said Letters Patent is hereby corrected as shown below:

Column 9 in Table I, No. 19, third column, "0.005" should read --0.008--; Table I, No. 26, last column, "60" should read --59--; Table I, No. 27, last column, "61" should read --60--; Table 1, No. 28, last column, "59" should read --61--.

Column 11, table in Example 3, line 1, second column, "168.27" should read --168.17--.

In Claim 3 "$C_{1-2}$" should read --$C_{1-3}$--.

In Claim 7, line 4, "(2, 2-difluoro)" should read --(2, 2-(difluoro)--.

Signed and Sealed this

Twenty-fourth Day of April, 2001

Attest:

NICHOLAS P. GODICI

Attesting Officer     Acting Director of the United States Patent and Trademark Office

UNITED STATES PATENT AND TRADEMARK OFFICE
Certificate

Patent No. 6,110,961                                                                       Patented: August 29, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Helen Lung White, deceased, late of Chapel Hill, N.C. (US) by James White, executor; Morton Harfenist, Chapel Hill, N.C. (US); Eric Boros, Chapel Hill, N.C. (US); Dennis Heyer, Durham, N.C. (US); and James L. Kelley, Raleigh, N.C. (US).

Signed and Sealed this Fifth Day of June 2007.

JOSEPH K. MCKANE
*Supervisory Patent Examiner*
Art Unit 1626